(12) United States Patent
Auge, II et al.

(10) Patent No.: US 7,713,269 B2
(45) Date of Patent: May 11, 2010

(54) DEVICES FOR ELECTROSURGERY

(75) Inventors: Wayne K. Auge, II, Santa Fe, NM (US); Roy E. Morgan, San Jose, CA (US)

(73) Assignee: NuOrtho Surgical, Inc., Fall River, MA (US)

( * ) Notice: Subject to any disclaimer, the term of this patent is extended or adjusted under 35 U.S.C. 154(b) by 0 days.

(21) Appl. No.: 12/239,320

(22) Filed: Sep. 26, 2008

(65) Prior Publication Data
US 2009/0030410 A1 Jan. 29, 2009

Related U.S. Application Data

(60) Division of application No. 11/061,397, filed on Feb. 17, 2005, now Pat. No. 7,445,619, which is a continuation-in-part of application No. 10/486,739, filed as application No. PCT/US02/26277 on Aug. 15, 2002, now abandoned, said application No. 11/061,397 is a continuation-in-part of application No. 11/010,174, filed on Dec. 10, 2004, which is a continuation of application No. PCT/US03/18575, filed on Jun. 10, 2003, said application No. 11/061,397 is a continuation-in-part of application No. 11/006,079, filed on Dec. 6, 2004, which is a continuation-in-part of application No. PCT/US03/18116, filed on Jun. 6, 2003, said application No. 11/061,397 is a continuation-in-part of application No. 10/741,753, filed on Dec. 19, 2003, which is a continuation of application No. PCT/US02/19498, filed on Jun. 19, 2002, which is a continuation-in-part of application No. 09/885,749, filed on Jun. 19, 2001, now Pat. No. 6,547,794, said application No. 11/061,397 is a continuation-in-part of application No. 10/414,781, filed on Apr. 15, 2003, now Pat. No. 7,105,011, which is a division of application No. 09/885,749.

(60) Provisional application No. 60/545,097, filed on Feb. 17, 2004, provisional application No. 60/387,775, filed on Jun. 10, 2002, provisional application No. 60/387,114, filed on Jun. 6, 2002, provisional application No. 60/312,965, filed on Aug. 18, 2001, provisional application No. 60/272,955, filed on Mar. 2, 2001, provisional application No. 60/226,370, filed on Aug. 18, 2000.

(51) Int. Cl.
*A61B 18/14* (2006.01)

(52) U.S. Cl. .............................. 606/41; 606/45; 606/49

(58) Field of Classification Search .................... 606/41
See application file for complete search history.

(56) References Cited

U.S. PATENT DOCUMENTS 3,911,107 A   10/1975   Krezanoski
(Continued)

FOREIGN PATENT DOCUMENTS

GB                  2037920       *   7/1980
(Continued)

OTHER PUBLICATIONS

Babincova, Melania et al., "High-Gradient Magnetic Capture of Ferrofluids: Implications for Drug Targeting and Tumor Embolization", *Zeitschrift fur Naturforschung* vol. 56-C 2001, 909-911.
(Continued)

*Primary Examiner*—Lee S Cohen
(74) *Attorney, Agent, or Firm*—Janeen Vilven; Vidal A. Oaxaca; Peacock Myers, P.C.

(57) ABSTRACT

Devices for electrosurgery by means of oxy-hydro combustion and methods for use of such devices in electrosurgical procedures. Provided are devices for combustion of oxygen and hydrogen, or other hydrocarbon fuels, wherein oxygen and hydrogen may be generated by electrolysis or oxygen and hydrogen, or other hydrocarbon fuels, may be supplied, such devices including an ignition source and an adjustable and translatable sheath for controlling such reactions. Also provided is a detachable and positionable sheath for controlling reactions and minimizing tissue damage with conventional electrosurgery devices.

3 Claims, 13 Drawing Sheets

U.S. PATENT DOCUMENTS

| | | | |
|---|---|---|---|
| 3,941,135 A | 3/1976 | von Sturm et al. | |
| 3,982,017 A | 9/1976 | Thiele | |
| 4,014,777 A | 3/1977 | Brown | |
| 4,105,017 A | 8/1978 | Ryaby et al. | |
| 4,266,532 A | 5/1981 | Ryaby et al. | |
| 4,266,533 A | 5/1981 | Ryaby et al. | |
| 4,504,493 A | 3/1985 | Marshall et al. | |
| 4,540,409 A * | 9/1985 | Nystrom et al. | 604/349 |
| 4,615,347 A * | 10/1986 | Schooley | 132/212 |
| 4,872,865 A | 10/1989 | Bloebaum et al. | |
| 4,938,970 A | 7/1990 | Hustead et al. | |
| 4,971,068 A | 11/1990 | Sahi | |
| 5,014,699 A | 5/1991 | Pollack et al. | |
| 5,236,456 A | 8/1993 | O'Leary et al. | |
| 5,282,861 A | 2/1994 | Kaplan | |
| 5,304,724 A | 4/1994 | Newton | |
| 5,314,476 A | 5/1994 | Prewett et al. | |
| 5,352,463 A | 10/1994 | Badylak et al. | |
| 5,360,440 A | 11/1994 | Andersen | |
| 5,366,443 A | 11/1994 | Eggers et al. | |
| 5,403,825 A | 4/1995 | Lagarde et al. | |
| 5,458,596 A | 10/1995 | Lax et al. | |
| 5,494,538 A | 2/1996 | Kirillov et al. | |
| 5,498,259 A | 3/1996 | Mourant et al. | |
| 5,514,130 A | 5/1996 | Baker | |
| 5,516,533 A | 5/1996 | Badylak et al. | |
| 5,554,141 A * | 9/1996 | Wendler | 604/352 |
| 5,569,242 A | 10/1996 | Lax et al. | |
| 5,584,863 A | 12/1996 | Rauch et al. | |
| 5,622,725 A | 4/1997 | Kross | |
| 5,669,904 A | 9/1997 | Platt et al. | |
| 5,669,907 A | 9/1997 | Platt et al. | |
| 5,669,934 A | 9/1997 | Sawyer | |
| 5,683,366 A | 11/1997 | Eggers et al. | |
| 5,697,281 A | 12/1997 | Eggers et al. | |
| 5,697,536 A | 12/1997 | Eggers et al. | |
| 5,697,882 A | 12/1997 | Eggers et al. | |
| 5,697,909 A | 12/1997 | Eggers et al. | |
| 5,741,261 A | 4/1998 | Moskovitz et al. | |
| 5,746,896 A | 5/1998 | Shimamune et al. | |
| 5,749,895 A | 5/1998 | Sawyer et al. | |
| 5,788,976 A | 8/1998 | Bradford | |
| 5,800,385 A | 9/1998 | Demopulos et al. | |
| 5,820,583 A | 10/1998 | Demopulos et al. | |
| 5,824,015 A | 10/1998 | Sawyer | |
| 5,840,166 A | 11/1998 | Kaneko | |
| 5,855,608 A | 1/1999 | Brekke et al. | |
| 5,860,950 A | 1/1999 | Demopulos et al. | |
| 5,871,469 A | 2/1999 | Eggers et al. | |
| 5,885,292 A | 3/1999 | Moskovitz et al. | |
| 5,919,191 A | 7/1999 | Lennox et al. | |
| 5,955,514 A | 9/1999 | Huang et al. | |
| 5,964,968 A | 10/1999 | Kaneko | |
| 6,032,077 A | 2/2000 | Pomeranz | |
| 6,033,654 A | 3/2000 | Stedronsky et al. | |
| 6,086,585 A | 7/2000 | Hovda et al. | |
| 6,112,122 A | 8/2000 | Schwardt et al. | |
| 6,117,109 A | 9/2000 | Eggers et al. | |
| 6,135,998 A | 10/2000 | Palanker | |
| 6,149,620 A | 11/2000 | Baker et al. | |
| 6,159,194 A | 12/2000 | Eggers et al. | |
| 6,162,219 A | 12/2000 | Nilsson et al. | |
| 6,174,309 B1 | 1/2001 | Wrublewski et al. | |
| 6,206,878 B1 | 3/2001 | Bishop et al. | |
| 6,213,999 B1 | 4/2001 | Platt et al. | |
| 6,214,003 B1 | 4/2001 | Morgan et al. | |
| 6,224,592 B1 | 5/2001 | Eggers et al. | |
| 6,235,024 B1 | 5/2001 | Tu | |
| 6,241,723 B1 | 6/2001 | Heim et al. | |
| 6,241,753 B1 | 6/2001 | Knowlton | |
| 6,264,650 B1 | 7/2001 | Hovda et al. | |
| 6,264,652 B1 | 7/2001 | Eggers et al. | |
| 6,273,883 B1 | 8/2001 | Furumoto | |
| 6,293,942 B1 | 9/2001 | Goble et al. | |
| 6,306,134 B1 | 10/2001 | Goble et al. | |
| 6,309,387 B1 | 10/2001 | Eggers et al. | |
| 6,322,549 B1 | 11/2001 | Eggers et al. | |
| 6,350,276 B1 | 2/2002 | Knowlton | |
| 6,383,184 B1 | 5/2002 | Sharkey | |
| 6,391,025 B1 | 5/2002 | Weinstein et al. | |
| 6,416,509 B1 | 7/2002 | Goble et al. | |
| 6,419,815 B1 | 7/2002 | Chambers et al. | |
| 6,461,352 B2 | 10/2002 | Morgan et al. | |
| 6,463,336 B1 | 10/2002 | Mawhinney | |
| 6,471,993 B1 | 10/2002 | Shastri et al. | |
| 6,547,794 B2 | 4/2003 | Auge | |
| 6,558,382 B2 | 5/2003 | Jahns et al. | |
| 6,772,013 B1 | 8/2004 | Ingle et al. | |
| 6,780,178 B2 | 8/2004 | Palanker et al. | |
| 6,824,555 B1 | 11/2004 | Towler et al. | |
| 6,832,995 B1 | 12/2004 | Towler et al. | |
| 6,890,332 B2 | 5/2005 | Truckai et al. | |
| 6,902,564 B2 | 6/2005 | Morgan et al. | |
| 7,066,932 B1 | 6/2006 | Morgan et al. | |
| 7,105,011 B2 | 9/2006 | Auge | |
| 7,354,438 B2 | 4/2008 | Morgan et al. | |
| 7,445,619 B2 | 11/2008 | Auge et al. | |
| 7,549,989 B2 | 6/2009 | Morgan et al. | |
| 2001/0007940 A1 | 7/2001 | Tu et al. | |
| 2002/0165596 A1 | 11/2002 | Wilson | |
| 2003/0028189 A1 | 2/2003 | Woloszko et al. | |
| 2003/0216732 A1 | 11/2003 | Truckai et al. | |
| 2003/0216733 A1 | 11/2003 | McClurken et al. | |
| 2004/0167244 A1 | 8/2004 | Auge, II | |
| 2004/0267255 A1 | 12/2004 | Auge, II et al. | |
| 2005/0085806 A1 | 4/2005 | Auge, II et al. | |
| 2005/0182449 A1 | 8/2005 | Auge, II et al. | |

FOREIGN PATENT DOCUMENTS

| | | |
|---|---|---|
| WO | WO02/102438 | 12/2002 |
| WO | WO03/015865 | 2/2003 |
| WO | WO03/103521 | 12/2003 |

OTHER PUBLICATIONS

Brennetot, R. et al., "Investigation of Chelate Formation, Intramolecular Energy Transfer and Luminescence Efficiency and Lifetimes in the Euthenoyltrifluoroacetone-trioctylphosphine oxide-Triton x-100 System Using Absorbance, Fluorescence and Photothermal Measurements", *Spectrochim Acta Part A* 2000, 703-715.

Chen, S. S. et al., "Heat-Induced Changes in the Mechanics of a Collagenous Tissue: Isothermal, Isotonic Shrinkage", *Transactions of the ASME* vol. 120 1998, 382-388.

Edwards, Ryland B. et al., "Thermometric Determination of Cartilage Matrix Temperatures During Thermal Chondroplasty: Comparison of Bipolar and Monopolar Radiofrequency Devices", *Arthroscopy* vol. 18 No. 4 2002, 339-346.

Fink, Bernd et al., "Holmium: YAG Laser-Induced Aseptic Bone Necroses of the Femoral Condyle", *Arthroscopy: The Journal of Arthroscopic and Related Surgery* vol. 12 No. 2 1996, 217-223.

Gould, Stephen E. et al., "Cellular Contribution of Bone Graft to Fusion", *Journal of Orthopaedic Research* vol. 18 2000, 920-927.

Grant, Kyle M. et al., "Magentic Field-Controlled Microfluidic Transport", *Journal of Americal Chemical Society* vol. 124 No. 3 2002, 462-467.

Ito, Takayasu et al., "Sensitivity of Osteoinductive Activity of Deminerlization and Defatted Rat Femur to Temperature and Duration of Heating", *Clinical Orthopaedics and Related Research* No. 316 1995, 267-275.

Janzen, Dennis L. et al., "Osteonecrosis After Contact Neodymium: Yttrium Aluminum Garnet Arthroscopic Laser Meniscectomy", *AJR 169* 1997, 855-858.

Lopez, Mandi J. et al., "Effects of Monopolar Radiofrequency Energy on Ovine Joint Capsular Mechanical Properties", *Clinical Orthopaedics and Related Research*, No. 374 2000, 286-297.

Medvecky, Michael et al., "Thermal Capsular Shrinkage: Basic Science and Clinical Applications", *Arthroscopy* vol. 17 No. 6 2001, 624-635.

Minczykowski, Andrzej et al., "Effects of Magnetic Resonance Imaging on Polymorphonuclear Neutrophil Adhesion", *Diagnostics and Medical Technology, Medical Science Monitor* vol. 7 No. 3 2001, 482-488.

Mourant, Judith R. et al., "Improvements in Laser "Welding" of Chicken Bone Tibias in vitro", *Laser Sciences and Applications Group*, Los Alamos, NM, 1-8.

Mourant, Judith R. et al., "Laser Welding of Bone: Successful in vitro Experiments", *Laser Sciences and Applications Group*, Los Alamos, NM, 1-5.

Rozbruch, S. R. et al., "Osteonecrosis of the Knee Following Arthroscopic Laser Meniscectomy", *Arthroscopy: The Journal of Arthroscopic and Related Surgery* vol. 12 No. 2 1996, 245-250.

Thal, Raymond et al., "Delayed Articular Cartilage Slough: Two Cases Resulting From Holmium: YAG Laser Damage to Normal Articular Cartilage and a Review of the Literature", *Arthroscopy: The Journal of Arthroscopic and Related Surgery* vol. 12 No. 1 1996, 92-94.

Torchilin, Vladimir P. et al., "Drug Targeting", *European Journal of Phamaceutical Sciences 11 Suppl 2* 2000, S81-S91.

Wall, Michael S. et al., "Thermal Modification of Collagen", *J. Shoulder Elbow Surg.* vol. 8 No. 4 1999, 339-344.

Wallace, Andrew L. et al., "Electrothermal Shrinkage Reduces Laxity but Alters Creep Behavior in a Lapine Ligament Model", *J. Shoulder Elbow Surg.* vol. 10 No. 1 2001, 1-6.

Zhang, Min et al., "Effect(s) of the Demineralization Process on the Osteoinductivity of Demineralization Bone Matrix", *J. Periodontol* 1997, 1085-1092.

Zohar, Ofer et al., "Thermal Imaging of Receptor-Activated Heat Production in Single Cells", Biophysical Journal vol. 74 1998, 82-89.

* cited by examiner

DEVICES FOR ELECTROSURGERY

CROSS-REFERENCE TO RELATED APPLICATIONS

This application is a divisional application of U.S. patent Ser. No. 11/061,397, entitled Devices for Electrosurgery, filed on Feb. 17, 2005, issued as U.S. Pat. No. 7,445,619 on Nov. 4, 2008, which is a continuation-in-part application of U.S. patent application Ser. No. 10/486,739, entitled Methods and Devices for Electrosurgery, filed on Aug. 24, 2004 now abandoned, which in turn was a national stage entry pursuant to 35 U.S.C. §371 of International Application Serial No. PCT/US02/26277, entitled Methods and Devices for Electrosurgery, filed on Aug. 15, 2002, which claimed priority to U.S. Provisional Patent Application Ser. No. 60/312,965, entitled System and Method of Electrosurgical Biologic Tissue Modification and Treatment Utilizing Oxy-Hydro Combustion—Acid Base Shift Reactions, filed on Aug. 15, 2001.

U.S. application Ser. No. 11/061,397 is a continuation-in-part application of U.S. application Ser. No. 10/119,671, entitled Methods and Devices for Electrosurgery, filed on Apr. 9, 2002, issued as U.S. Pat. No. 6,902,564 on Jun. 7, 2005, which claimed priority to U.S. Provisional Application Ser. No. 60/312,965, entitled System and Method of Electrosurgical Biologic Tissue Modification and Treatment Utilizing Oxy-Hydro Combustion—Acid Base Shift Reactions, filed on Aug. 15, 2001.

U.S. application Ser. No. 11/061,397 is also a continuation-in-part application of U.S. application Ser. No. 11/010,174, entitled Methods for Electrosurgical Electrolysis, filed on Dec. 10, 2004, which in turn was a continuation application of International Application Serial No. PCT/US03/18575, entitled Methods and Devices for Electrosurgical Electrolysis, filed on Jun. 10, 2003, which claimed priority to U.S. Provisional Patent Application Ser. No. 60/387,775, entitled Methods and Devices for Electrosurgical Electrolysis, filed on Jun. 10, 2002.

U.S. application Ser. No. 11/061,397 is a continuation-in-part application of U.S. application Ser. No. 11/006,079, entitled Methods and Devices for Electrosurgery, filed on Dec. 6, 2004, which in turn was a continuation-in-part application of International Application Serial No. PCT/US03/18116, entitled Methods and Devices for Electrosurgery, filed on Jun. 6, 2003, which claimed priority to U.S. Provisional Patent Application Ser. No. 60/387,114, entitled Methods and Devices for Electrosurgery, filed on Jun. 6, 2002, and to U.S. Provisional Patent Application Ser. No. 60/387,775, entitled Methods and Devices for Electrosurgical Electrolysis, filed on Jun. 10, 2002.

U.S. application Ser. No. 11/061,397 is a continuation-in-part application of U.S. application Ser. No. 10/414,781, entitled Method For Achieving Tissue Changes In Bone Or Bone-Derived Tissue, filed on Apr. 15, 2003, issued as U.S. Pat. No. 7,105,011 on Sep. 12, 2006, which in turn was a divisional application of U.S. Pat. No. 6,547,794, entitled Methods for Fusing Bone During Endoscopy Procedures, issued on Apr. 15, 2003, and filed as U.S. Ser. No. 09/885,749 on Jun. 19, 2001, which claimed priority to U.S. Provisional Patent Application Ser. No. 60/226,370, entitled Method For Fusing Bone During Endoscopy Procedures, filed on Aug. 18, 2000, and of U.S. Provisional Patent Application Ser. No. 60/272,955, entitled Method For Fusing Bone During Endoscopy Procedures, filed on Mar. 2, 2001.

U.S. application Ser. No. 11/061,397 is a continuation-in-part application of U.S. application Ser. No. 10/741,753, entitled Methods and Compositions for Fusing Bone During Endoscopy Procedures, filed on Dec. 19, 2003, which in turn was a continuation application of International Application No. PCT/US02/19498, International Publication No. WO 02/102438, entitled Methods and Compositions For Fusing Bone During Endoscopy Procedures, filed on Jun. 19, 2002, which in turn was a continuation-in-part application of U.S. Pat. No. 6,547,794, entitled Methods for Fusing Bone During Endoscopy Procedures, issued on Apr. 15, 2003, and filed as U.S. Ser. No. 09/885,749 on Jun. 19, 2001, which claimed priority to U.S. Provisional Patent Application Ser. No. 60/226,370, entitled Method For Fusing Bone During Endoscopy Procedures, filed on Aug. 18, 2000, and of U.S. Provisional Patent Application Ser. No. 60/272,955, entitled Method For Fusing Bone During Endoscopy Procedures, filed on Mar. 2, 2001.

U.S. application Ser. No. 11/061,397 also claims the benefit of the filing of U.S. Provisional Patent Application Ser. No. 60/545,097, entitled Devices for Electrosurgery, filed on Feb. 17, 2004. The Specification and claims thereof of each of the foregoing is incorporated herein by reference.

BACKGROUND OF THE INVENTION

1. Field of the Invention (Technical Field)

The present invention relates to devices for electrosurgery, including devices that operate by means of oxygen and hydrogen combustion, and methods utilizing such devices.

2. Description of Related Art

Note that the following discussion refers to a number of publications by author(s) and year of publication. Discussion of such publications herein is given for more complete background and is not to be construed as an admission that such publications are prior art for patentability determination purposes.

A variety of electrosurgical devices, used for cutting, ablation, and the like in surgical procedures, are known. In general, it is claimed that these devices utilize mechanisms of action based on various plasma formation physiochemical paradigms. A plasma, broadly defined as "the fourth state of matter" as opposed to solids, liquids, and gases, is a state in which atoms have been broken down to form free electrons and stripped nuclei by the application of high energy or temperatures (ca. $10^6$ degrees). In a plasma, the charge of the electrons is balanced by the charge of the positive ions so that the system as a whole is electrically neutral. The energy input required to initiate a plasma is related to the initial state of the matter as a solid, liquid, or gas, the molecular bond energy, and the ease with which electrons can be stripped from their orbits, among other variables. The percent of the samples that actually become a plasma is usually very small due to the large energy requirements to create a plasma (i.e. ~0.1% of a mole). Further, a plasma can be constrained by magnetic fields lowering the input energy necessary. A sustainable plasma often requires a vacuum or magnetic field control since the plasma elements quickly seek to be grounded, quenching the plasma; however, some systems may form short duration plasmas on the order of nano- or micro-seconds depending upon energy input and degree of vacuum/magnetic field present.

Some prior art references disclose electrosurgical devices with claimed use of a gas plasma consisting of an ionized gas that is capable of conducting electrical energy. In certain of these devices, either ambient air or a supplied gas is used for ionization, such as the devices disclosed in U.S. Pat. Nos. 5,669,904, 6,206,878 and 6,213,999. If a gas is supplied, it is an inert gas such as argon. In general, these devices are intended for use in ambient atmosphere for the treatment of soft tissue.

Other electrosurgical devices function in liquid media and utilize some form of radiofrequency (RF) energy, such as with two or more electrodes. Heat is generated by use of the RF energy, resulting in destruction or ablation of tissues in proximity to the electrodes. Thus the devices may be employed for coagulation of blood vessels, tissue dissection, tissue removal, and the like. U.S. Pat. No. 6,135,998 teaches an electrosurgical probe immersed in liquid media or tissue, wherein an electrical pulse is applied, with the claimed result that "plasma streamers" are formed from the endface area of a first electrode. In this patent, it is claimed that cutting action results from the plasma streamers. The minimum voltage is on the order of 1.5-2.0 kV, with 15 kV being the preferred maximum voltage, at a minimum power dissipation of 500 Watts, and preferable a higher power dissipation of 800 to 1500 Watts.

Other lower energy electrosurgical devices are known, consisting of monopolar and bipolar configurations that function at energy configurations at or below 1.4 kV and 300 Watts. Both monopolar electrosurgical devices, in which the electrosurgical device includes an active electrode with a return electrode separately connected to the patient such that direct electric current flows through the patient's body, and bipolar electrosurgical devices, in which the electrosurgical device includes both active and return electrodes, are now well known in the art. These electrosurgical device configurations can be used in ambient air or in a fluid medium. In general, it has been believed that these electrosurgical devices generally operate by means of creation of a plasma or some related form of ionization. Thus prior art devices, such as that disclosed in U.S. Pat. No. 5,683,366, are claimed to rely on the fluid irrigant components participating in ionic excitation and relaxation, with attendant release of photonic energy. This mode of operation is often referred to as "utilizing a plasma". Prior art methods claiming an ionized vapor layer or plasma include, in addition to the patents disclosed above, the methods disclosed in U.S. Pat. Nos. 5,697,882, 6,149,620, 6,241,723, 6,264,652 and 6,322,549, among others.

A plasma requires that atoms be completely ionized to a gas of positive ions and electrons, and, if sustainable, would likely need to occur in a vacuum-like environment. It is unlikely that many, if not most, prior art devices generate a plasma even for a short time. This most notably follows from consideration of the overall energy balance required to initiate or sustain a plasma in either ambient air or aqueous, cellular, or other biologic environments. The nominal 200 to 1500 Watts of power normally employed in a typical electrosurgical device, or any other energy level or configuration contemplated for electrosurgical application (most, however, are between 200 and 300 Watts), is insufficient to initiate and/or sustain a plasma, even in a vacuum and with magnetic field control, even for a short period of time. For example, in a saline solution typically utilized during electrosurgery, 49.6 kW-s/mole (I eV=5.13908; II eV=47.2864; III eV=71.6200; etc.) is needed to ionize sodium, while the ionization energy of simple water is 12.6206 eV (i.e. one electron volt=$1.602177 \times 10^{-19}$ Joules) as referenced in *CRC Handbook of Chemistry and Physics*, 72 ed., Lide, David R., CRC Press, 1991. The energy to initiate a plasma typically exceeds the ionization potential of a material, and to sustain a plasma requires an even greater energy input. Further, once ions have been formed in solution, such as in an aqueous solution of sodium as employed in electrosurgery, a yet even greater energy input is required.

Further, many prior art electrosurgical references ignore recognized phenomena relating to plasmas, such as the large ionization potentials and energy necessary to initiate a plasma or to sustain a plasma and the role of the vacuum or magnetic fields in such circumstances. Most electrosurgical devices cannot deliver the energy required to initiate, let alone sustain, a plasma; and, further, electrosurgical applications do not occur in a vacuum environment or in a magnetically controlled environment. The energy needed to create a plasma in vivo during electrosurgery would overwhelm the ability of the host organism to withstand such an energy insult globally. Plasma cutters as used in metal fabrication are examples of the high energy necessary to "utilize a plasma" at normal pressures; yet such high energy levels certainly have not been contemplated for electrosurgical application due to the significant iatrogenic damage that would occur. This understanding has led us to search for other physiochemical paradigms to understand electrosurgery as it is practiced at energy configurations amenable and safe for in vivo application and to more fully and correctly explain common physiochemical observations during electrosurgery in order to create more appropriate electrosurgical devices and methods.

In industrial settings, it is known to employ an oxygen and hydrogen combustion reaction, such that a "water torch" results by ignition of co-mingled oxygen and hydrogen gas molecules liberated from water through high frequency electrolysis, as is disclosed in U.S. Pat. No. 4,014,777. However, such methods have never been intentionally applied to medical procedures, such as for electrosurgical devices and methods. Further, such devices and methods have never been optimized for the constraints of use of electrosurgical devices on biologic tissue, including constraints resulting from the presence of discrete quantities of electrolyte fluids, the presence of physiologic fluids and materials, the desires to minimize collateral tissue injury, the need to avoid generation of toxic by-products, the attendant host organism tissue response, and the like.

There is thus a need for electrosurgical devices that are optimized to the true physical and chemical processes involved in the operation and use of such electrosurgical devices upon biologic tissue within this energy spectrum and power range.

BRIEF SUMMARY OF THE INVENTION

In one embodiment, the invention provides an apparatus for electrosurgery, the apparatus including a probe with a distal end and a proximal end, the proximal end forming a handle for holding the probe; first and second gas delivery channels disposed within probe; a gas mixing plenum chamber with an inlet and an outlet at the distal end of the probe, the first and second gas delivery channels being in fluid connection with the inlet; an ignition source proximal to the gas mixing plenum chamber outlet; a cylindrical sleeve positioned around the distal end of the probe; and, an adjustably positionable actuator disposed on the handle and translatably connected to the cylindrical sleeve, such that the cylindrical sleeve can be longitudinally translated relative to the distal end of the probe, thereby forming a cavity of variable volume about the distal end of the probe. The ignition source may include an active electrode, which may optionally be battery powered, and which serves to initiate combination of the first and second gases. In the embodiment wherein the ignition source includes an active electrode, the cylindrical sleeve may be an electrically insulating sleeve, optionally wherein the cylindrical sleeve extends distally beyond the active electrode, such as extending distally between about 1 mm and about 40 mm beyond the active electrode. Further in the embodiment wherein the ignition source includes an active electrode, the apparatus can include at least one return electrode.

The apparatus may further include least one detector proximal to the distal end of the probe and within the cavity of variable volume for detecting a parameter relating to oxyhydro combustion. Such detector may detect one or more of pH concentration, temperature, conductivity, ionic concentration, consumption of oxygen or hydrogen, sound, or changes in local pressure. The apparatus can thus further include a detection circuit for receiving a parameter detected by the at least one detector.

Where the ignition source includes an active electrode, the apparatus can further include a control circuit providing an output control signal controlling an amount of power output to the at least one active electrode in response to an output from a detection circuit for receiving a parameter detected by at least one detector disposed proximal to the distal end of the probe and within the cavity of variable volume for detecting a parameter relating to oxy-hydro combustion.

In the apparatus there can further be provided a self-regulating thermal quenching portal system comprising at least one opening for introducing an aqueous fluid to gas mixing plenum chamber. In yet another embodiment, there can be provided a flame arrester positioned between the gas mixing plenum chamber outlet and the active electrode.

In another embodiment, the invention provides a movable sheath adapted for use with a conventional radiofrequency (RF) electrosurgical probe, the sheath including a generally cylindrical plenum with an open first end and an open second end and of a diameter such that the open second end may be co-axially placed over the electrode end of an RF electrical probe, whereby the open first end extends beyond the electrode end of the RF electrical probe; and a flexible polymeric fixation sleeve for securing the position of the generally cylindrical plenum to the RF electrosurgical probe. In one embodiment of the sheath, the generally cylindrical plenum includes a plurality of perforations. The flexible polymeric fixation sleeve of the sheath can be fixed to the generally cylindrical plenum, and the flexible polymeric fixation sleeve can include a plurality of demarcations for determining the position of the movable sheath with respect to the electrode end of the RF electrical probe.

In yet another embodiment, there is provided an apparatus for electrosurgery including a probe with a distal end and a proximal end; a concave plenum chamber on the distal end of the probe with an active electrode disposed therein, the active electrode providing for electrolysis of an aqueous medium into hydrogen and oxygen and ignition of such hydrogen and oxygen; and a circumferential insulated leading edge on the concave plenum chamber on the distal end of the probe for sealing contact with tissue to be treated. The leading edge can include a sharpened edge for sealing contact with tissue, or alternatively a roughened edge for sealing contact with tissue. The apparatus can further include a return electrode on the proximal side of the circumferential insulated leading edge and disposed on an exterior surface of the probe.

A primary object of the present invention is to provide an electrosurgical device that regulates the rate of combustion in underwater environments, such as combustion in aqueous, cellular and biologic environments.

Another object of the present invention is to provide an electrosurgical device that provides tissue dissection, ablation and the like by means of an oxy-hydro combustion reaction.

Another object of the present invention is to provide a device and methods that eliminate the need for use of an ionic solution, such as saline, to foster oxy-hydro combustion reactions at the surgical site.

Another object of the present invention is to provide for oxy-hydro combustion that utilizes the salt ion fluid of intracellular structures.

Another object of the present invention is to provide devices employing low energy levels to achieve ignition of oxygen and hydrogen gases, such ignition and subsequent combustion providing the desired tissue dissection, ablation and the like.

Another object of the present invention is to provide an electrosurgical device with lower energy requirements, thereby resulting in a lower net energy transfer to local tissue structures, whereby there are lower levels of collateral tissue damage.

Another object of the present invention is to provide an electrosurgical device that provides combustion gases, such as oxygen and hydrogen, as part of the electrosurgical device.

Another object of the present invention is to provide an electrosurgical device that provides oxygen and hydrogen combustion gases by hydrolysis, with ignition of the resulting combustion gases, with the plenum further including a sharp-edged plenum chamber leading edge to enhance contact of the plenum to tissue and prevent contact of tissue with the zone of oxygen and hydrogen combustion.

Another object of the present invention is to provide an electrosurgical device that provides for combustion of gases, such as oxygen and hydrogen, and further includes one or more portals to draw in ambient fluid to partially quench the combustion reaction, thereby reducing the net heat of reaction and additionally reducing the thermal requirements of the flame ejection nozzle.

Another object of the present invention is to provide an electrosurgical device that can operate on either alternating current (AC) or direct current (DC), and that does not require an unequal current density as a distinguishing feature between a first electrode and a second electrode.

A primary advantage of the present invention is the ability to optimize ionic salt solutions for the oxy-hydro combustion reaction.

Another advantage of the present invention is the utilization of an acid-base throttle effect to regulate an electrosurgical device.

Another advantage of the present invention is the use of a wide range of different and novel salt solutions, in addition to the normal saline conventionally employed in electrosurgical procedures.

Another advantage of the present invention is that devices and methods are provided that do not require an unequal current density between a first electrode and second electrode, and may effectively operate with equal current densities, optionally for electrolysis of an aqueous medium into oxygen and hydrogen, and additionally for initiation of combustion of oxygen and hydrogen, where the oxygen and hydrogen is generated by electrolysis or is externally provided.

Another advantage of the present invention is that devices and methods are provided that require lower energy levels and further lower current densities than do prior art electrosurgical devices, such energy levels and current densities being only such as are required to initiate combustion of oxygen and hydrogen (or a hydrocarbon gas) and optionally for electrolysis of an aqueous medium into oxygen and hydrogen.

Another advantage of the present invention is that it provides for the use of feedback loop control algorithms to govern electrical motors or other actuating means to position the movable insulating sheath member, in response to the degree of electrolysis or combustion desired.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

The invention disclosed herein provides electrosurgical devices that operate in conductive media, such as an ionic aqueous media. The electrosurgical devices employ combustion, and preferably oxygen and hydrogen (oxy-hydro) combustion, as a mechanism for tissue dissection, ablation, cutting, coagulation, modification, treatment and the like. In one embodiment, an external source of oxygen or hydrogen, and preferably both, may be utilized. Electrical energy, such as a high frequency voltage difference, and preferably radiofrequency energy, can be employed to initiate oxy-hydro combustion and, in the embodiments so requiring, induce electrolysis of the media within which it functions or of the tissue to which it is applied to achieve the desired goals of electrosurgical treatment.

Figure 1A:
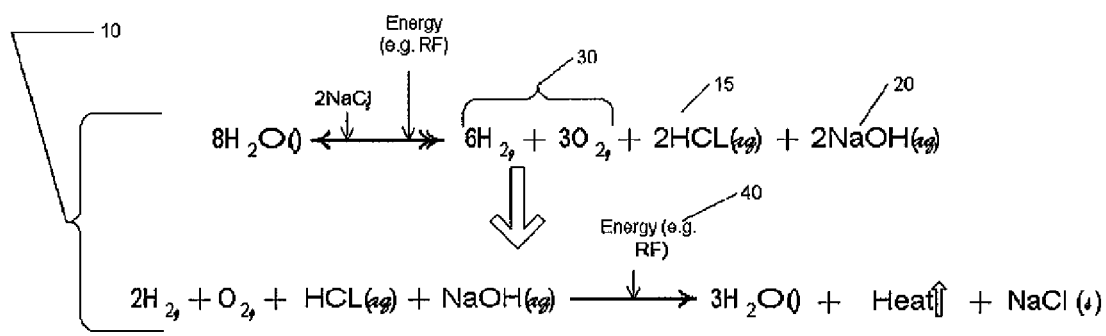
FIG. 1A is the stoichiometric chemical equation for chemical reactions related to the invention.

The equations of FIG. 1A illustrate the chemical equations that describe the overall oxy-hydro reaction, with associated acid-base shifts, resulting from hydrolysis of water and subsequent ignition of the resulting oxygen and hydrogen as disclosed herein. It is hypothesized that what has been traditionally thought of as the ordinary phenomenon of electrosurgery, namely "arcing", "electron excitation", "molecular friction", "vapor layer", "plasma formation", "plasma streamers", or "popping", may more properly be understood to be a result, in at least substantial part, of oxy-hydro combustion occurring within biologic constraints. The physiochemistry of the electrosurgical process is hypothesized to consist of an acid-base shift that governs the relative availability of the amount of water that can be consumed as part of a hydrolysis chemical reaction. The hydrolysis reaction is driven by the high frequency current flowing between active and return electrodes in both the bi-polar and mono-polar modes of operation of electrosurgical probes. This oxy-hydro combustion theory accounts for all necessary chemical and energy constituents that are present as well as the physical observations of light emission and heat generation during the use of such devices. The physiochemical occurrences of electrosurgery have not previously been reconciled into a single accurate and cohesive theory.

Chemical equations 10 generally govern the process herein disclosed, whereby the initial liberation of elemental oxygen and hydrogen gases 30 occurs by means of electrolysis. Given that the underwater electrosurgical process occurs in a salt solution, either externally applied or that of the tissue or cell itself, such as a 0.9% by weight saline solution, the true role of these elements should also be reconciled. The presence and true action of the salt, i.e. sodium chloride (NaCl) for example, can be accounted for by means of equations 10. The normal stoichiometry of the electrolysis reaction dictates that if elemental gas separation is occurring, then the solute participants must join with the remaining solution components of water to form a complementary acid-base pair. This pair is shown on the right-hand side of the upper half of equations 10 as hydrochloric acid 15 and sodium hydroxide 20 base pair. As is well known, hydrogen and oxygen gases 30 can be co-mingled without spontaneous exothermic reaction. A small amount of energy, such as RF energy 40, is required to overcome the nominally endothermic reaction and ignite the oxy-hydro combustion. Once ignited, the reaction will continue until all the reactants are consumed and reduced to the products shown on the right-hand side of the lower half of equations 10.

Figure 1B:
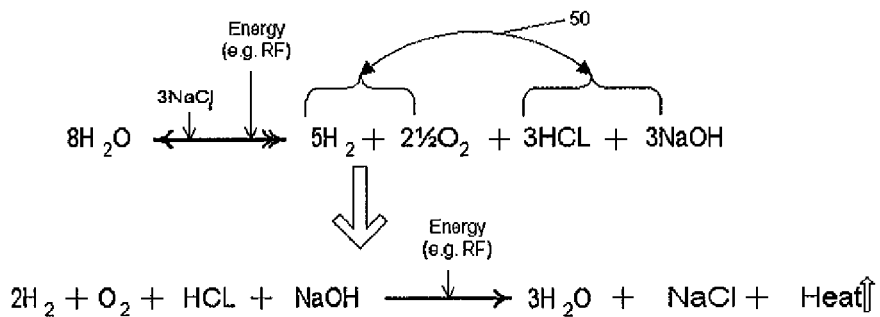
FIG. 1B is the equation for the acid-base "throttle" effect.

The equations of FIG. 1B illustrate the effect of the acid-base throttling reaction herein disclosed. The oxy-hydro combustion process depicted is dynamic and occurs in a fixed fluid reservoir, which necessarily results in dynamically changing concentrations of salt ions as a function of electrolytic conversion of water to elemental gas. This equation necessarily suggests that as the acid-base shift occurs in the reservoir, less and less water is available for hydrolysis. This phenomenon is seen in FIG. 1B where the acid-base pair is shown in increased molar proportion to the normal stoichiometric quantity of base reactions 10. The reduction of available water for hydrolysis is evident in the relationship 50 of oxygen and hydrogen gas to the acid-base pair. The finding is necessarily evident from the stoichiometry, namely that insufficient water is available given a fixed initial eight (8) moles of water, based on the finite reservoir of water, with increasing resulting molar concentrations of acid and base as oxygen and hydrogen are liberated from the solution in a gaseous state, such as by bubbling out of solution. As fewer moles of oxygen and hydrogen gas are present after hydrolysis as in FIG. 1B, the balancing portion of atoms account for the dynamic increase acid-base concentration.

Figure 1C:
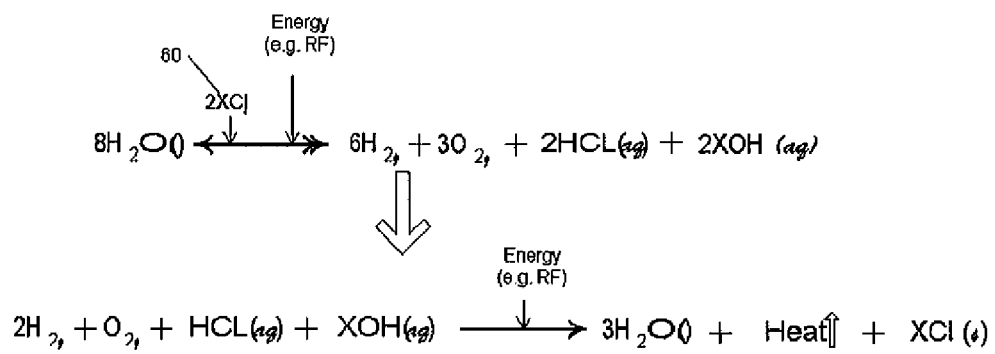
FIG. 1C is the equation for a generalized form of the oxy-hydro reaction process.

The equations of FIG. 1C demonstrate a more general case of the oxy-hydro combustion reaction process in which the ionic salt is represented by variable 60, where X is any appropriate group I, period 1-7 element of the periodic table. This generalized reaction illustrates how hydronium and hydroxide ions can contribute to the same overall chemical reaction known as oxy-hydro combustion.

Figure 1D:
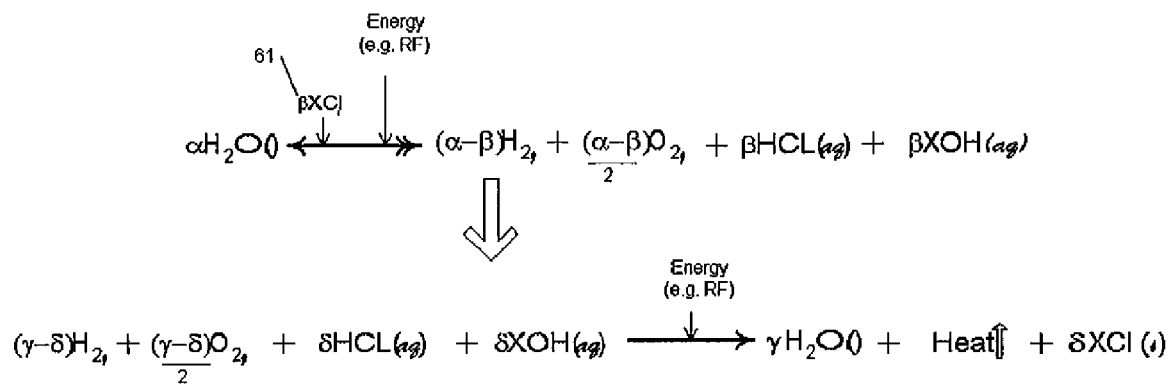
FIG. 1D is the equation for a generalized form of the oxy-hydro reaction process showing the effect of varying molar coefficients.

The equations of FIG. 1D demonstrate the more general case of the oxy-hydro combustion reaction process in which the ionic salt is represented by variables 61 of $\alpha$, $\beta$, $\gamma$, and $\delta$, wherein the molar quantities required for stoichiometric combustion are any value that appropriately satisfies the oxidation reduction valence requirements for the overall reaction. This generalized reaction case shows how oxygen and hydrogen requirements can vary and still result in the same overall chemical reaction known as oxy-hydro combustion.

The modes of oxy-hydro combustion operation described in FIG. 1A, FIG. 1B and FIG. 1C depict theoretical stoichiometric reaction processes induced by application of high frequency electromagnetic energy to a salt ion solution, including salt ion solutions typically found within biologic tissues themselves. The fundamental process is governed by the rate of electrolysis in the initial dissociation of water into oxygen and hydrogen gas, as shown in equations 10.

Without wishing to be bound by theory, it is believed that the mechanism of action explaining operation of prior art electrosurgical devices is erroneous, and that an understanding and appreciation of the herein hypothesized correct mechanism of action results in devices and methods as further disclosed herein.

In prior art, it has been assumed that conventional bipolar electrosurgical devices utilize excitation and relaxation of salt ions resulting in photonic energy release such as through a plasma formation. The basis for such claims is that sufficient energy is imparted to the vaporized salt solution to provide electron shell excitation of the native sodium ions. Upon relaxation of the excited electron, a photon is emitted (a foundational concept of quantum theory as originally developed by Niels Bohr in 1913). However, the ionization energy per mole of Na is 496 kJ as referenced in the *CRC Handbook of Chemistry and Physics*, 72 ed., Lide, David R., CRC Press, 1991, pp. 210-211. This energy is the equivalent to 496,000 Watt-seconds/mole. Even if only one-tenth of a mole of Na is present, a net energy of 49.6 kW-s/mole is needed to ionize the sodium to form a plasma. This energy is far greater than the 200 to 1500 Watts of power provided by prior art conventional electrosurgical power supplies, methods, and devices.

Further, monopolar electrosurgical devices have been described as using a "molecular friction" phenomenon to generate an "arc." The implicit assumption of this paradigm is that the majority of the energy imparted by the wave/particle function of nominal waves created by the electrosurgical power supply and device is absorbed at the natural frequency of the salt ions. A process called "ionic agitation" to produce molecular friction, resulting from ions attempting to "follow" the changes in direction of alternating current, is used as one common description of the observed phenomenon as referenced in M. J. Medvecky, et al., Thermal Capsular Shrinkage Basic Science and Applications, *Arthroscopy: The Journal of Arthroscopic and Related Surgery,* 2001; 17:624-635. However, ordinary microwave technology demonstrates that higher frequencies are needed to excite water, including salt water, as well as the ions normally contained within biologic tissue. Additionally, understanding how ions from a salt exist in solution makes it unlikely that the claimed excitations result in the observed phenomenon. A normal saline solution consists of sodium chloride (NaCl) salt dissolved in water, conventionally ~0.9% NaCl by weight for normal saline. Classical solute-solvent theory states that the salt (solute) will dissociate in water (solvent) to form NaOH and HCl in equilibrium. Thus the actual energy is not absorbed by a "salt" ion at all, but rather by the acid-base equilibrium ions in coexistence within the solution media.

From these examples, it is hypothesized, again without wishing to be bound by theory, that many of processes heretofore described as resulting from a "plasma" actually are a result, at least in part, of oxy-hydro combustion. The oxygen and hydrogen are created by electrolysis, with concurrent ignition, all as a result of high frequency, high voltage energy sources. The invention disclosed herein correctly explains the phenomenon heretofore described during electrosurgery observations as "arcing", "electron excitation", "molecular friction", "vapor layer", "plasma formation", "plasma streamers", or "popping". The understanding and appreciation of this disclosed mechanism of action enables further electrosurgical device and method embodiments that more accurately follow in vivo physiochemical processes and open such embodiments to new applications not previously envisioned for electrosurgical devices and methods as disclosed heretofore.

The modes of electrolysis and oxy-hydro combustion operation described in FIG. 1A, FIG. 1B and FIG. 1C depict theoretical stoichiometric reaction processes induced by application of high frequency electromagnetic energy to a salt ion solution, including salt ion solutions typically found within biologic tissues themselves. The fundamental process is governed by the rate of electrolysis in the initial dissociation of water into oxygen and hydrogen gas, as shown in equations 10. Based upon this understanding, methods and devices for electrosurgery can be developed that utilize (1)

one or (2) the other, or (3) both of the electrosurgical constituent reactions known as electrolysis and oxy-hydro combustion as herein disclosed.

For example, oxy-hydro combustion can be utilized for therapeutic procedures like cutting, ablation, coagulation, vaporization, and other related procedures that are similar to those previously disclosed in the prior art. The oxy-hydro combustion reaction delivers the energy configuration necessary to cause these tissue effects and the host responses thereof as desired and described in those procedures. Electrosurgical methods and devices used for these types of procedures (see U.S. Pat. Nos. 5,669,904, 6,206,878, 6,213,999, 6,135,998, 5,683,366, 5,697,882, 6,149,620, 6,241,723, 6,264,652, 6,322,549, 6,306,134, 6,293,942, and other patents to similar effect) presumptively utilize this reaction, despite the lack of recognition in such patents that the occurrence of electrolysis and oxy-hydro combustion is at least a primary effecter in these types of procedures (rather than plasma or related forms of Ionizing radiation). In essence, prior art methods and devices have been developed to achieve specific and interrelated treatment goals without fully understanding the physiochemical occurrences of electrosurgery as practiced. An inherent risk in such a situation is the possibility that iatrogenic harm and complication may occur related to the use of such methods and devices. Most notably these iatrogenic complications are due to the inability to fully contain the energy application of electrosurgery to tissue based upon the limited understanding of the physiochemical processes that are occurring. Unfortunately, since the use of such methods and devices have been increasing as electrosurgical techniques have become more popular and indications for use have been expanding, some practitioners and researchers have called for the guarded use of electrosurgical technology until further investigation can be completed. See, for example, "Thermometric determination of cartilage matrix temperatures during thermal chondroplasty: comparison of bipolar and monopolar radiofrequency devices." Arthroscopy. 2002 April; 18(4):339-46.

The treatment methods and devices of the prior art rely upon the common denominator of tissue necrosis as the means to accomplish these treatment goals; and, this tissue effect is the main parameter employed to categorize prior art electrosurgery as a means to achieve tissue cutting, ablation, coagulation, vaporization, and the like. Most peer-reviewed studies have evaluated level of necrosis, depth of necrosis, or related parameters to quantify electrosurgical effects for these types of treatment procedures as such evaluation are most relevant in those treatment settings. Tissue necrosis occurs to some degree in all methods in the prior art due to their desired goals of tissue cutting, ablation, coagulation, vaporization, and the like. This necrosis is typified histologically by karyorrhexis or nuclear picnosis at one end of the spectrum and frank necrosis or vaporization at the other end followed by host responses directed to the specific level of necrosis induced by the manner of tissue treatment.

Electrolysis as the initial functional reaction of electrosurgery, on the other hand, has not been explicitly recognized or exploited in the prior art for therapeutic procedures. The methods and devices developed in the prior art to achieve the treatment goals of cutting, ablation, coagulation, vaporization, and the like, have been generated without the knowledge of electrolysis as a relevant constituent part of the electrosurgical physiochemical process. This circumstance further clarifies the motivation of prior art to limit methods and devices to cutting, ablation, coagulation, vaporization, and the like that require the higher energy configurations that induce oxy-hydro combustion. Based upon this realization, methods and devices designed to provide or augment the supply of the constituents of the oxy-hydro combustion as disclosed herein can bypass the relative need of electrolysis for therapeutic procedures designed to accomplish such related treatment goals as cutting, ablation, coagulation, and vaporization yet in a more expedient and efficient manner. One of the major motivations for these methods and devices, as herein, is to decrease tissue electrolysis for these types of treatment procedures since electrolysis induced in tissue itself is very detrimental to tissue cellular structures. It induces not only tissue necrosis quite dramatically but also transfers other significant collateral physiochemical effects that are not necessary and are additionally problematic for the treatment goals of cutting, ablation, coagulation, vaporization, and the like, as will be discussed below. These collateral effects often delay or impair healing responses of the surrounding areas of tissue treatment, expanding the depth of necrosis as described witnessed in prior art electrosurgical applications and peer-reviewed assessments. The methods, devices and means as disclosed herein provide for limiting electrolysis-related detrimental tissue effects witnessed during the electrosurgical procedures of cutting, ablation, coagulation, vaporization, and the like that are realized through the understanding of the physiochemical occurrences of electrosurgery. Tissue changes and responses thereof are more fully recognized and characterized allowing additional novel uses for the oxy-hydro combustion phenomenon. In one such embodiment, tissue contact with the working electrode(s) of the instrument probe can be eliminated via the use of a translating sheath that can contain the constituents of the relevant electrosurgical reactions and place the active electrode(s) away from the tissue surface. This procedure as disclosed herein benefits the tissue in that the location of electrolysis and oxy-hydro combustion occurrences is shifted from that within the tissue itself (as contemplated and practiced in prior art since the probe electrodes are used to contact the tissue to exert its effects) to that within the surrounding fluid. This shift can be partial or complete based upon the desired tissue effects of electrolysis and oxy-hydro combustion at the treatment locale. In this way, tissue electrolysis can be marginalized as a relevant occurrence in the cutting, ablation, coagulation, and vaporization treatment methods that utilize oxy-hydro combustion.

Based upon the foregoing, the following is apparent: First, in those instances where it is desirable to induce tissue cutting, ablation, coagulation, or vaporization by electrosurgical means (i.e. high energy tissue necrosis and removal), the occurrence of electrolysis in any form may be irrelevant to the procedure goals, and thus oxy-hydro combustion serves as the relevant effecter of the procedure. This may be conveniently done by means of the methods and devices provided herein, including by means of externally supplied oxygen and nitrogen, by means of partially externally supplied combustion elements, such as by means of a hydrogen-liberating electrode, or by means of electrolysis. Second, in those instances where oxy-hydro combustion is desired and tissue electrolysis is not, such as when collateral tissue damage is to be avoided, the methods and devices of as provided herein can be employed with oxy-hydro combustion as the effecter of the procedure. Third, in those instances where tissue electrolysis is desired and oxy-hydro combustion is not, i.e. a lower energy transfer to tissue is desired, the methods and devices disclosed herein can be employed. Fourth, in those instances where the effects of electrosurgical electrolysis are desired without tissue electrolysis or oxy-hydro combustion, the methods and devices disclosed herein can be utilized.

It is thus hypothesized that current art electrosurgical processes, presumably through failure to recognize these processes as effecting tissue electrolysis and oxy-hydro combustion, have effectively been designed and implemented such that inducing various levels of tissue necrosis in the form of cutting, ablation, coagulation, vaporization, and host responses thereof results. The methods and devices as disclosed herein can be employed to decrease tissue electrolysis and its associated detrimental collateral physiochemical effects.

In one embodiment of the invention, the devices and method of this invention include a means to deliver one or more gases required for combustion to a surgical site, without the need to perform electrolysis to liberate hydrogen and/or oxygen for the combustion process. In one preferred embodiment, both oxygen and hydrogen gases are provided for the combustion process, with ignition through electrode means. The gases may be in a compressed form, and optionally are metered via throttling valves and mixing chambers. The gases, such as oxygen and hydrogen, delivered via a suitable conduit to an electrosurgical device. The gases are delivered to the distal end of said device where they are ignited using a voltage source and an ignition device. The resulting combustion zone is sufficiently controllable to enable treatment of small biological structures and sufficiently scalable to permit treatment of comparatively large areas.

The devices of the invention described herein may be employed with any of a wide variety of tissues, including without limitation any soft tissue or hard tissue, or soft tissue-derived and bone-derived products and/or materials. In the case of collagen tissues, the methods and devices can further be employed to fuse, weld or otherwise join such tissues such as for bone welding, vascular anastomosis, neurorraphy, and the like. Further, as acid-base shifts affect cell membrane permeability, such changes can be harnessed for therapeutic measures, as disclosed in U.S. patent application Ser. No. 10/486,739.

It may further be seen that certain embodiments of the invention described herein may be employed in applications where prior art conventional monopolar devices are employed, such as in a non-conductive aqueous media of some endoscopy fluids. Even where the macro-environment, such as endoscopy fluids, is non-conductive, the micro-environment, in proximity to the electrodes and devices hereafter described and the biological tissues to be modified, is necessarily conductive. Thus the methods and devices described herein may, with such modifications as are required and will be apparent to one of skill in the art, be employed in applications where prior art conventional monopolar devices are now employed. Similarly, the methods and devices described herein may be employed in applications where prior art conventional bipolar devices are employed, such as environments wherein a conventional conductive aqueous media is employed. Further, the methods and devices described herein may be employed in applications of traditional open surgical procedures, i.e. in ambient air (versus endoscopic procedures), with the host biologic tissue itself serving as the fluid reservoir or fluid environment.

The devices of this invention can be employed with a variety of solutions, including 0.9% NaCl, 0.9% KCl, $H_2SO_4$, HCl, distilled $H_2O$, and a glycine solution, and a variety of state parameters, including varied pH and temperature. Further, the devices and methods of this invention have been employed without solutions in the macro sense, and been use in "ambient" air conditions of hydrated and normal biologic tissue. In addition, a variety of RF energy settings have been employed, such as the embodiment of 150-2000 Volts peak to peak with a range of power settings between 5 and 500 Watts. Based on analysis of various solutions, states, and energy profile applications, the general equation of FIG. 1C was validated, and data obtained for the graph of FIG. 5. Although the energy input required to initiate and/or sustain a plasma markedly exceeds these levels (or any levels contemplated for electrosurgical application), even for the most favorable plasma generating conditions (refer to above ionization discussion for typically encountered constituents of a biologic system during electrosurgery), the transition from electrolysis and combustion to that of plasma formation based upon energy input has not been determined. It is anticipated that as energy level is increased, significantly surpassing the ionization potentials of the constituents of a biologic system, electrolysis and combustion would yield to plasma formation; however, this transition point far exceeds the levels of energy that an organism can withstand and is not contemplated for electrosurgery due to the significant iatrogenic injury that would be induced. The energy configurations typically employed in and contemplated for electrosurgery, and those that we have verified as discussed above, provide sufficient energy to initiate and sustain the electrolysis and combustion reactions as disclosed in U.S. patent application Ser. No. 10/486,739, allowing for the use of such physiochemical reactions for therapeutic means as disclosed in U.S. patent application Ser. No. 10/486,739.

The devices described in FIGS. 4 through 9 do not employ electrolysis to produce hydrogen and gas with concurrent ignition of the oxy-hydrogen flame at the point of electrolysis. Rather, in one preferred embodiment these devices employ gas canisters, which may be miniature canisters disposed within the handle of the device. At least one of these canisters contains oxygen and at least one other canister contains a gas that may be employed in combustion; hydrogen is a preferred gas, but other gases may be employed, including preferably gases wherein one or more carbon atoms are present, such as methane, acetylene or other gases. In an alternative embodiment, oxygen and hydrogen may be stored within a confined matrix material. In yet another embodiment, the devices may include a container for electrolysis, such that within the handle or another portion of the device there is contained a volume of liquid, such as saline solution, and one or more electrodes for electrolysis, the electrolysis producing oxygen and hydrogen, which oxygen and hydrogen transits the conduits provided and is ignited as provided in the following description. Depending on the power consumption characteristics of the electrode(s) employed for electrolysis, it may be necessary to employ a wire connecting the device(s) to a source of power sufficient for the intended purpose.

The devices described in FIGS. 4 through 9 further contain a source of electrical power, such as a battery, which may be a rechargeable battery, a fuel cell, or the like, producing sufficient power for operation of the electronic circuitry, if provided, and for ignition of the oxy-hydrogen mixture. In one embodiment, a fuel cell may be employed to produce electrical power. A proton exchange membrane type of fuel cell is employed, wherein hydrogen and optionally also oxygen is provided by means of one or more canisters, which canisters are also preferentially further employed for oxy-hydrogen combustion. Oxygen may alternatively be obtained from the atmosphere. Sufficient separate fuel cells are combined to form a fuel-cell stack producing the voltage required for the specific application.

Figure 4:
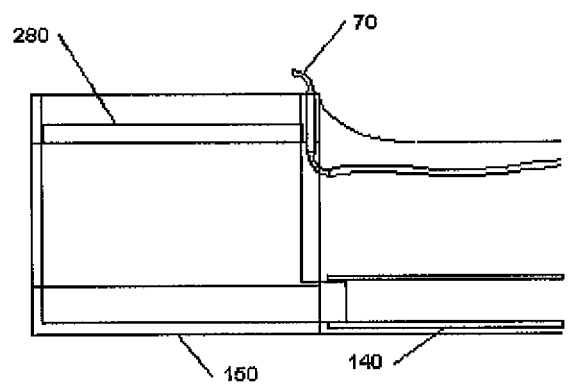
FIG. 4 is an illustration of a cordless oxy-hydro combustion probe of the invention, including gas storage containers (not depicted) and a source of electrical power (not depicted)
Figure 5:
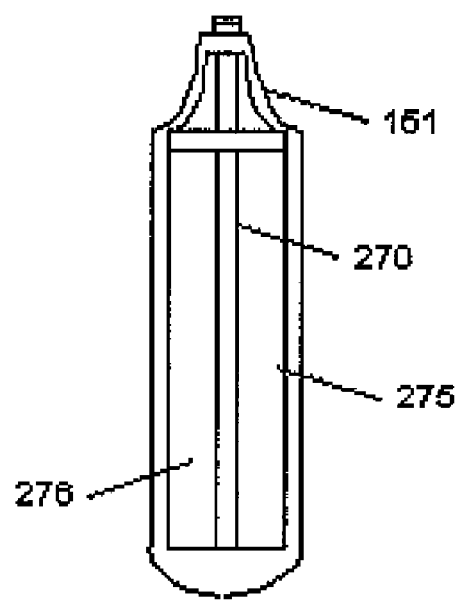
FIG. 5 is an illustration of a cordless oxy-hydro combustion probe of the invention, including gas storage containers (not depicted) and a source of electrical power (not depicted)
Figure 6:
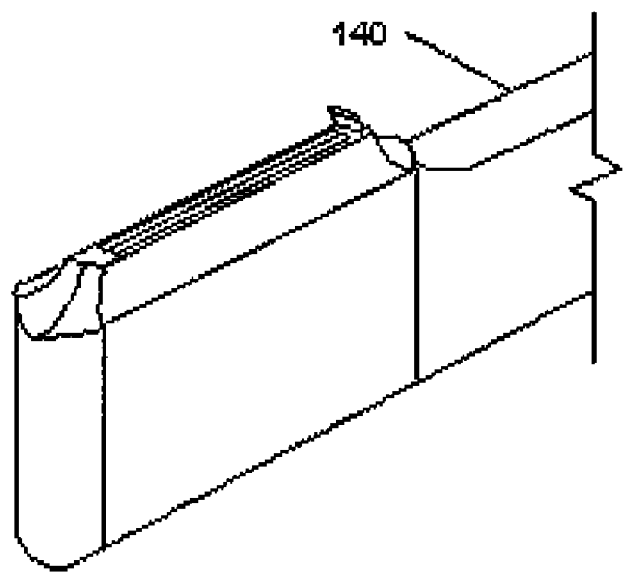
FIG. 6 is an illustration of a cordless oxy-hydro combustion probe of the invention, including gas storage containers (not depicted) and a source of electrical power (not depicted)

FIGS. 4 through 6 illustrate the use of a cordless oxy-hydro combustion probe useful for cutting all forms of tissue, including hard bony structures, without the necessary need for electrolysis of the media in which the probe functions and without the induction of internal tissue electrolysis, which is detrimental to tissue viability. Thus these devices may be employed for ablation, cutting, coagulation and/or vaporization of tissues. Independently isolated flow conduits 275, 276 are provided within primary lumen 140 separated by wall 270 and supplied to a fluid acceleration converging nozzle 151 whereby the independent gas constituents are accelerated to a turbulent state. As set forth above, the source(s) of gases are canisters, matrix material which releases gases, a hydrolysis chamber or the like. In a preferred embodiment, the source of gas is sufficiently small to be contained within the handle or adjacent portions of the device, such that the device can readily be held in one hand by the surgeon without connection, by wires or tubes, to any external structure. Upon exiting the independent conduits explosion protection is provided in the form of a spark or flame arrester 280 to prevent combustion propagation into the device. The co-mingled gases are ignited via electrode 70 (here functioning as an external igniter) to produce the oxy-hydrogen flame that is used to perform tissue operations. Probe tip 150 is manufactured so as to have a sharp leading edge as shown near the fluid flow exit portal for ancillary use as a mechanical sharp cutting device in addition to thermal and ablative characteristics normally exhibited by oxy-hydro tools.

Figure 8:
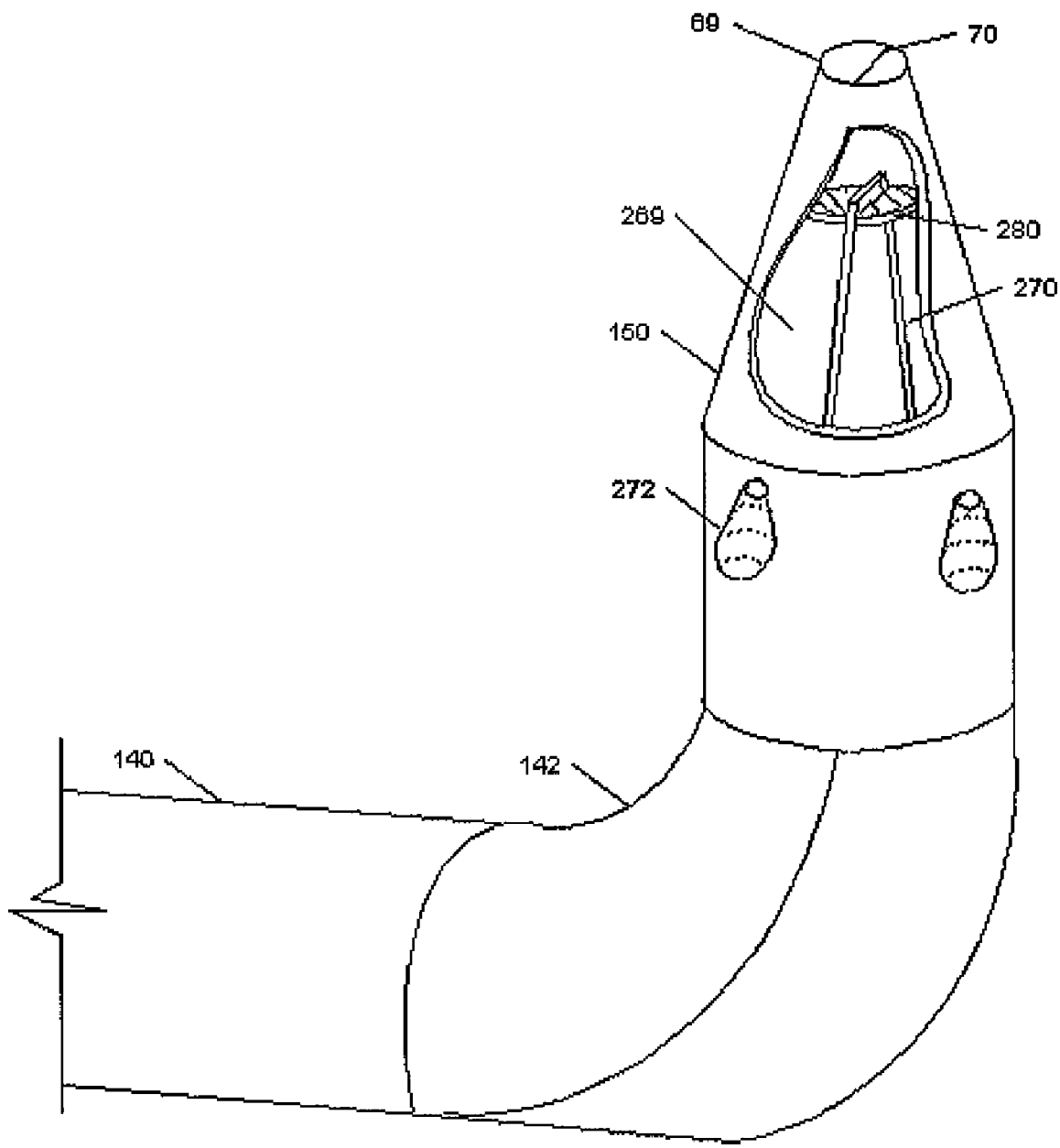
FIG. 8 is an illustration of a cordless oxy-hydro combustion probe of the invention utilizing a self-regulating automatic thermal quenching portal system, including gas storage containers (not depicted) and a source of electrical power (not depicted)

FIG. 8 illustrates a cordless oxy-hydro combustion device utilizing self-regulating automatic thermal quenching portal system 272. This portal system provides a means for the induction of surrounding fluid media at proportional rates to oxygen and hydrogen gas flow to maintain desired maximum flame temperatures at exit/ignition portal 69. This fluid induction is metered into the independent gas flow streams, which are separated by wall 270. This fluid induction is created by means of internal venturi section 142 providing gas acceleration which creates sub-ambient pressure at portal 272 inlets and subsequently drawing surrounding fluid into gas stream 269. This venturi section 142 may be provided at a variety of specified angles relative to primary lumen 140. Portal 272 provides calibrated orifice entry points into gas stream 269 at known volumetric flow rates, providing proportional mass-flow which acts as a heat sink within the oxy-hydro combustion reaction according to the first law of thermodynamics ($q = m \cdot Cp \cdot \Delta T$, where Cp is defined as the latent heat of vaporization for the surrounding fluid). The mass flow rate of surrounding fluid is calibrated by means of said entry portals to provide sufficient combustion quenching heat capacity to maintain safe and effective operational thermal discharge levels of exit/ignition portal 69. This ignition is created by electrode 70 (here functioning as an energy input filament). This ignition system (69, 70) is disposed within the distal insulating tip assembly 150, which may be made detachable from the venturi induction portion 142. The spark or flame arrester 280 acts as an additional fluid mixer/atomizer to ensure even dispersion of entrained surrounding fluid thereby providing additional means of evenly controlled combustion zone thermal variation.

Figure 9:
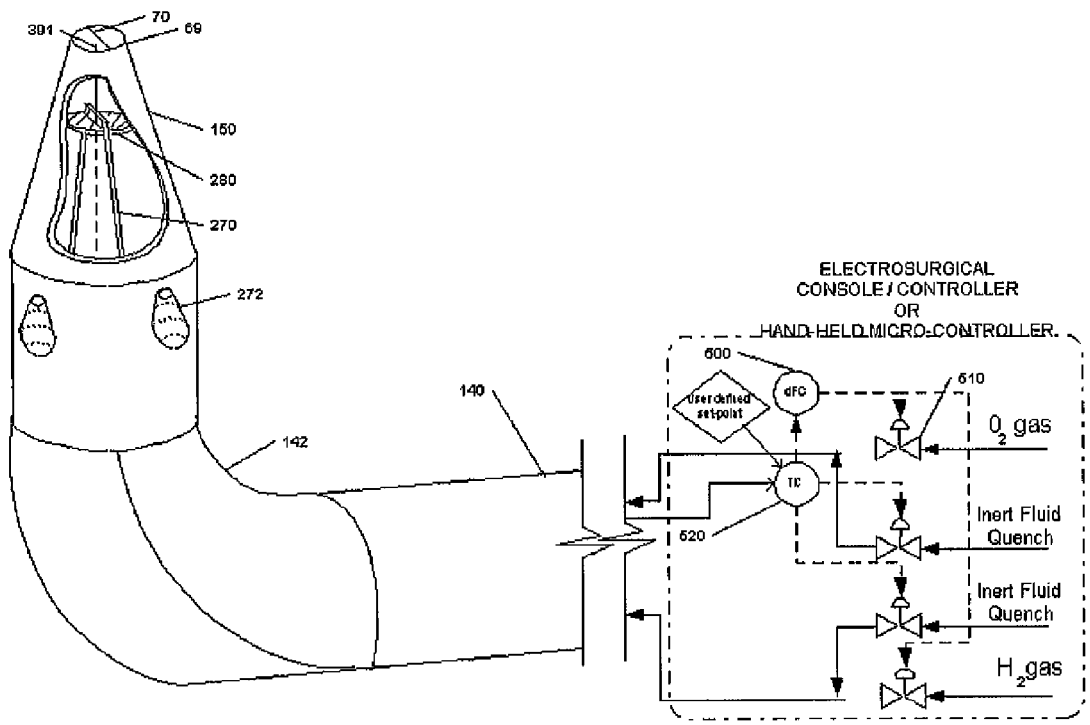
FIG. 9 is an illustration of control automation of a cordless oxy-hydro combustion probe of FIG. 8.

FIG. 9 illustrates the control automation to a cordless oxy-hydro combustion probe. Variable sensor 391 provides means for detecting combustion zone temperature and provides feedback signal to temperature controller 520. The temperature controller is configured as part of an overall fluid manifold gas quenching system, comprised of differential signal output controller 500, which supplies independent, proportional control signal to flow control valves 510 governing proportional flow of inert quench fluids to the primary oxygen and hydrogen gas flow streams. The proportional flows provide thermal combustion control at exit/ignition portal 69. Proportionality of the temperature controller 520 is governed by user-defined set points within the engineered limit span of the controller 520. The general function of the temperature controller 520 is to provide additional quench gas when the user defined set point is positioned for lower temperatures and to decrease the quench gas flow when the user defined set point is positioned for higher temperatures. The controller 520 has a 4-20 mA output proportioned to the combined released heat of reaction including heat lost due to absorption by inert non-reacting quench gases at the desired set point dialed in by the user. The structures defined by 70, 140, 142, 150, 270, 272, and 280 serve the same functions as in FIG. 8.

Figure 14:
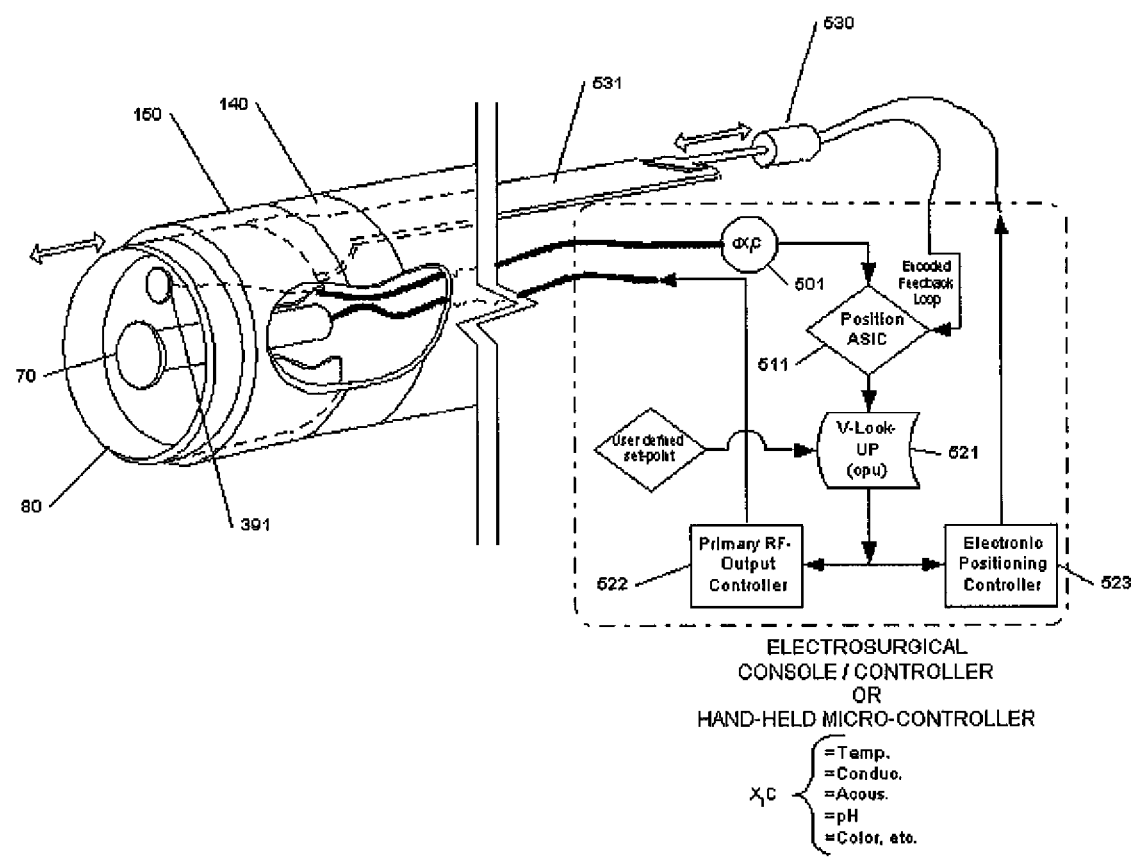
FIG. 14 is an illustration of a control mechanism for maintaining optical spacing of the active electrode relative to tissue structures and/or a translatable sheath.

FIG. 14 illustrates the automated control which provides a means for maintaining the optimal spacing of the active electrode 70, disposed distal from the primary lumen 140 which is simultaneously acting as the return electrode, from tissue structures being treated. Here too it is intended that the device be employed only so as to provide electrolysis only of the media or other interfacing agent, without electrolysis of tissues of the patient to be treated. Thus the design of the device of FIG. 14 is such that induction of tissue electrolysis by contact of the active electrode to the tissue is avoided. Further, combustion is itself limited, depending on the rate of electrolysis, and the therapeutic affect is largely a result of electrolysis of the media adjacent to, but not in contact with, tissues to be treated. Actuating arm 531, which in turn is driven by electric positioning motor 530, actuates translatable sheath 80. Translatable sheath thus can extend the insulating properties of insulator 150 beyond the profile or position of the active electrode 70, providing means to create a temporary localized chamber when the translatable sheath 80 is extended and brought into contact with tissue. Fluid field sensor 391 provides primary control variable feedback to differential controller 501 as analog input and is output via flip-flop AND conversion to a digital control signal for use by application-specific integrated circuitry logic controller 511, such as an FPGA, MOSFET, or similar intermediate digital logic gate controlling array. Flash RAM, and additional high level input/output governance, is controlled by CPU 521, utilizing software governed database lookup techniques, such as those commonly known in C+ or C++ programming code, to provide dual proportional output via Primary RF Output Controller/Generator 522; and further and optionally also to Electronic Positioning Controller 523 for simultaneous balanced positioning of translatable sheath 80 coupled to matched power setting through controller 522, providing the primary controlling input to match user set-point according to primary control variable known characteristics correlation to desired set point. Electrical power may be provided by wires connected to a suitable source of power, which may be one or more sources of power, such as a high voltage source for operation of the active electrode and a lower voltage source for operation of the circuits provided, or may alternatively be by means of a fuel cell or any other suitable source of electrical power.

Thus the device of FIG. 14 provides, in one embodiment, for the use of "feedback loop" control algorithms to govern the electrical motors or other actuating means to position or move the insulating sheath member, wherein one input for such control algorithms includes either the degree or rate of electrolysis (where the device provides for electrolysis) or the combustion rate of the oxygen and hydrogen (or other hydrocarbon fuel). Either the degree or rate of electrolysis, or alternatively the combustion rate, or both, may be set by a programmable setting, or alternatively may be a function of a third parameter measured by means of a sensor, such as gas production, temperature, etc.

Figure 7:
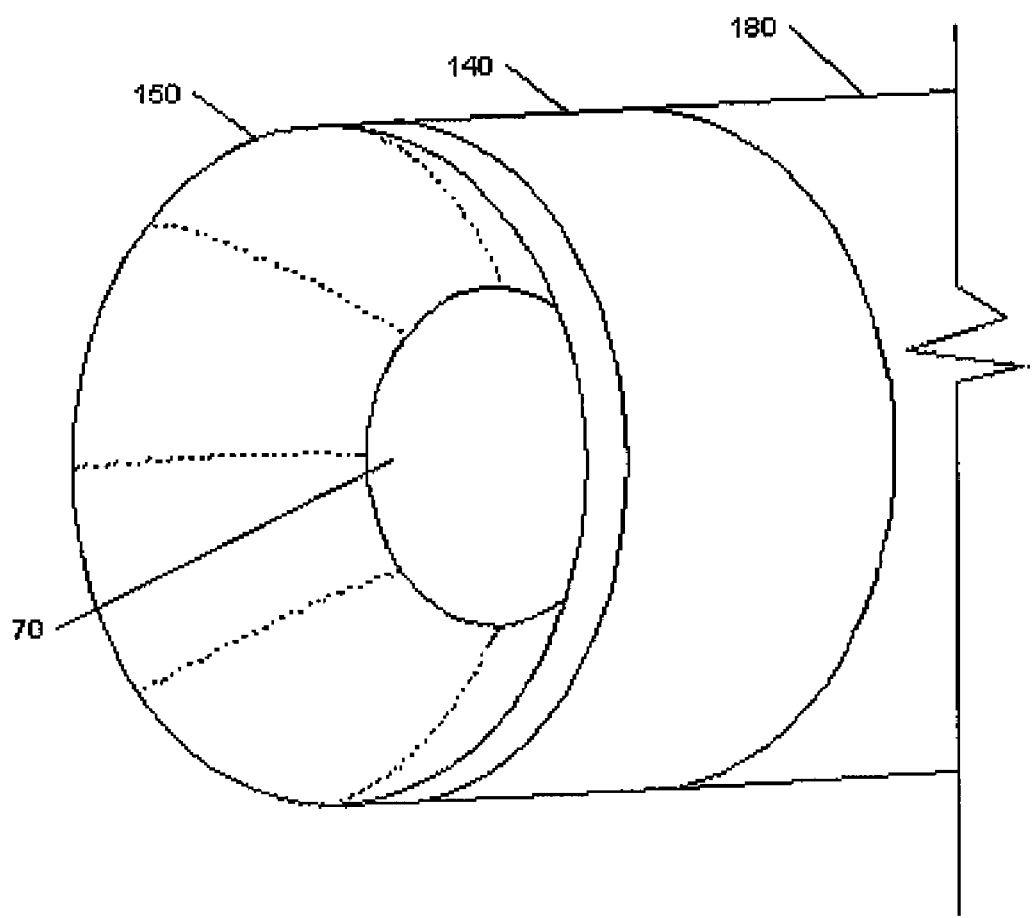
FIG. 7 is an illustration of a cordless oxy-hydro combustion probe of the invention, including gas storage containers not (depicted) and a source of electrical power (not depicted)

FIG. 7 illustrates the use of a fixed electrode insulator geometry optimized for use as an electrosurgical probe. In this device, electrolysis is induced by the electrode, with concomitant ignition of the hydrogen and oxygen gases. It is intended that the device be employed only so as to provide electrolysis only of the media or other interfacing agent, without electrolysis of tissues of the patient to be treated. Thus the design of the device of FIG. 7 is such that induction of tissue electrolysis by contact of the active electrode to the tissue is avoided. A second electrode, or return electrode, is provided and may be disposed on the probe, but is not depicted. Further, combustion is itself limited, depending on the rate of electrolysis, and the therapeutic affect is largely a result of electrolysis of the media adjacent to, but not in contact with, tissues to be treated. Insulator 150 is configured distal of primary lumen 140 (which simultaneously acts as the return electrode) whose surface area is limited by insulation 180 to provide means to maintain fixed tissue separation from active electrode 70. This spacing creates a reaction chamber for the electrosurgical reactions and creates a chamber between active electrode 70 and the leading edge of insulator 150 when insulator 150 is in contact with tissue. The leading edge of insulator 150 is provided with a semi-sharp or roughened edge to prevent inadvertent tissue "bulging" which may cause tissue contact with active electrode 70. This reaction chamber is typically filled initially with the fluid of the electrosurgical environment when in contact with adjunct tissue structures providing localization for the electrosurgical reactions to induce therapeutic benefits. The elimination of tissue contact with the active electrode eliminates the presence of internal tissue electrolysis which is detrimental to tissue viability. In the device of FIG. 7, either AC or DC current may be employed, and an unequal current density between a first electrode and second electrode, such as the active electrode and a return electrode, is not required. Thus the device of FIG. 7 may effectively operate with equal current densities between a first electrode and second electrode. Similarly, the device of FIG. 7 may operate at lower energy levels and further lower current densities than that required for prior art electrosurgical devices, such energy levels and current densities being only such as are required for electrolysis of an aqueous medium into oxygen and hydrogen and to initiate combustion of the oxygen and hydrogen so generated.

Figure 15:
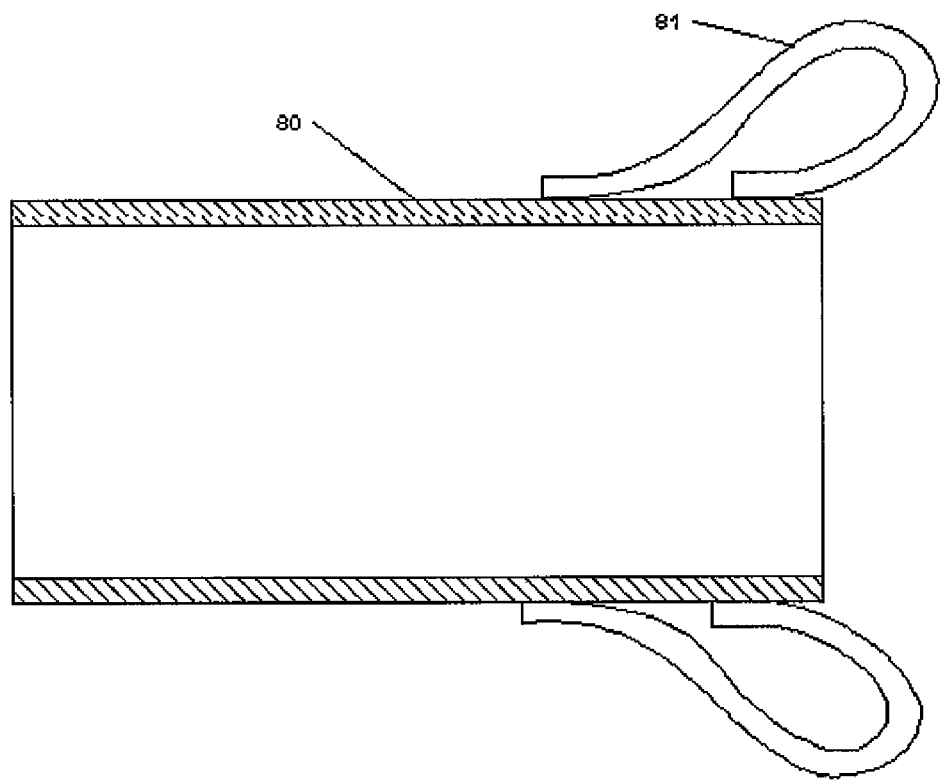
FIG. 15 is a side illustration of a detachable positioning sheath.
Figure 16:
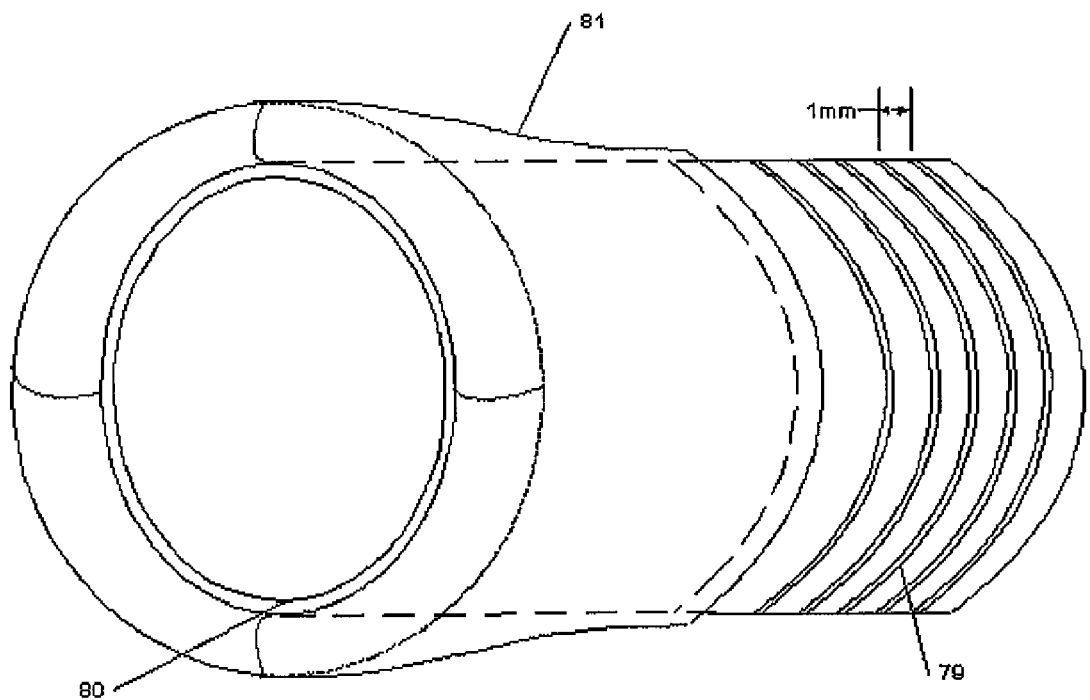
FIG. 16 is an illustration of a detachable positioning sheath.

FIGS. 15 and 16 illustrate a detachable positioning sheath. The devices of FIGS. 15 and 16, and similar devices, may be employed with prior art conventional RF electrosurgical devices or probes. Use of such art conventional devices results in tissue electrolysis at points where the electrode(s) contact the tissue, resulting in tissue necrosis and delayed wound healing. The sheaths of FIGS. 15 and 16, and similar devices, may be employed with such art conventional RF electrosurgical devices or probes, and result in positioning of the active electrode some distance from the tissue to be treated. In an appropriate aqueous media, the devices will induce electrolysis and, depending on the rate and volume of oxygen and hydrogen so produced, combustion of such gases. Thus energy transfer to the tissues is by means of an interfacing agent, such as a saline solution, with attendant reduced tissue necrosis and damage. Uses and applications of such therapeutic means are disclosed in U.S. patent application Ser. No. 10/486,739, incorporated here by reference. With respect to FIGS. 15 and 16, rigid cylindrical sheath 80, may be provided with perforations of various configurations without altering the fundamental principle of its function, and provides known spacing between tissue structures and electrosurgical probe active electrodes 70. This rigid sheath portion is positioned co-cylindrically on any electrosurgical probe that is not sheath enabled, thereby providing accurate spacing by means of demarcations 79. Flexible polymeric fixation sleeve 81 is unrolled onto primary lumen members of non-sheath enabled probes to provide fixation of the rigid sheath relative to probe active electrode position. Preferably the sleeve 81 is made from a translucent, and more preferably transparent, polymeric material. The sheath of FIGS. 15 and 16 can be repositioned intra-operatively through the use of forceps or manual unrolling to relocate rigid sheath portion 80. Rigid and flexible sheath portions may be adhesively bonded or ultra-sonically welded together to prevent relative translation and ensure accurate positioning throughout the entirety of procedural operations. Advantageously, the demarcations 79 provide distance graduations for accurate positioning of the sheath at a procedure-specific distance prior to insertion of the RF electrosurgical devices or probe with a sheath of this invention, such that adequate separation may be maintained between the probe or device end, and specifically an electrode thereof, and tissue to be treated.

Figure 2:
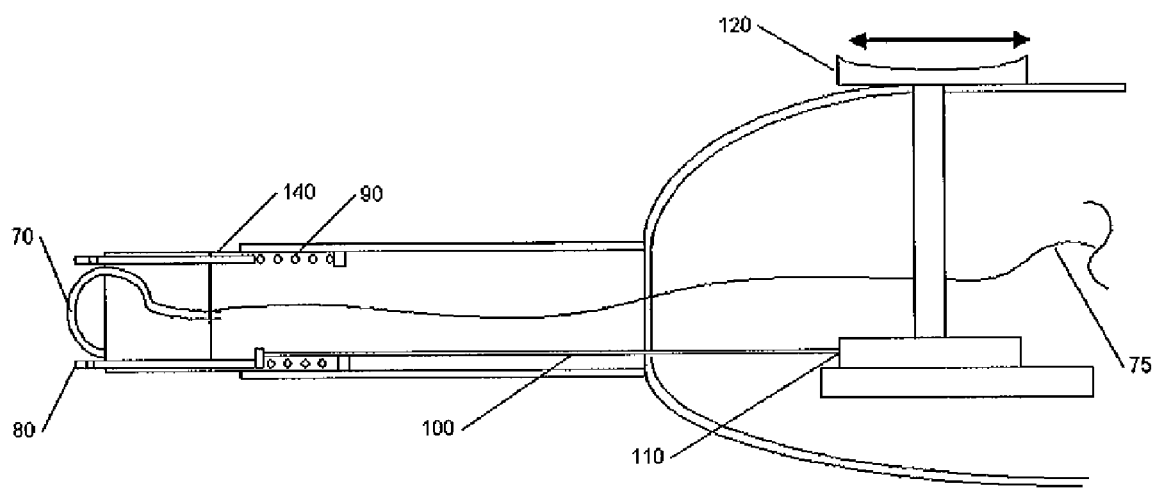
FIG. 2 is a view of an electrosurgical probe with a retractable sheath to create a fluid chamber that activates the acid-base throttle effect of oxy-hydro combustion in an aqueous ionic solution.

FIG. 2 is a view of a preferred embodiment of an acid-base throttle sheath probe used in the underwater, cellular and biologic electrosurgical environment. Translating sheath 80 is employed to create an acid-base trapping zone and thereby harness the acid-base "throttling" effect of lowering the available moles of electrolyzed oxy-hydrogen gas, thereby reducing the net heat of reaction in the oxy-hydro combustion. Translating sheath 80 extends itself beyond the most distal portion of active electrode 70 to form a plenum chamber wherein acid-base pairs are allowed to collect and decrease the reactants of oxy-hydro combustion. Current flows between active electrode 70 and return electrode 140 to complete the electrical circuit. Sheath 80 can be selectively positioned by using sliding ratcheting finger switch 120 via coupler guide stanchion 110 and push-rod 100 to set the desired quantity of acid-base entrapment and tune the rate of reaction observed at active electrode 70. Active electrode lead wire 75 is constructed to have sufficient slack within the probe body that translation of active electrode 70 is not constrained by connected lead wire 75. Sheath return spring 90 is tensioned by translation of push rod 100 as sheath 80 is extended to its most distal position, and is retained by finger switch ratcheting mechanism 120. When released, sheath 80 is pulled by return spring 90 into its normally proximal position.

Figure 3:
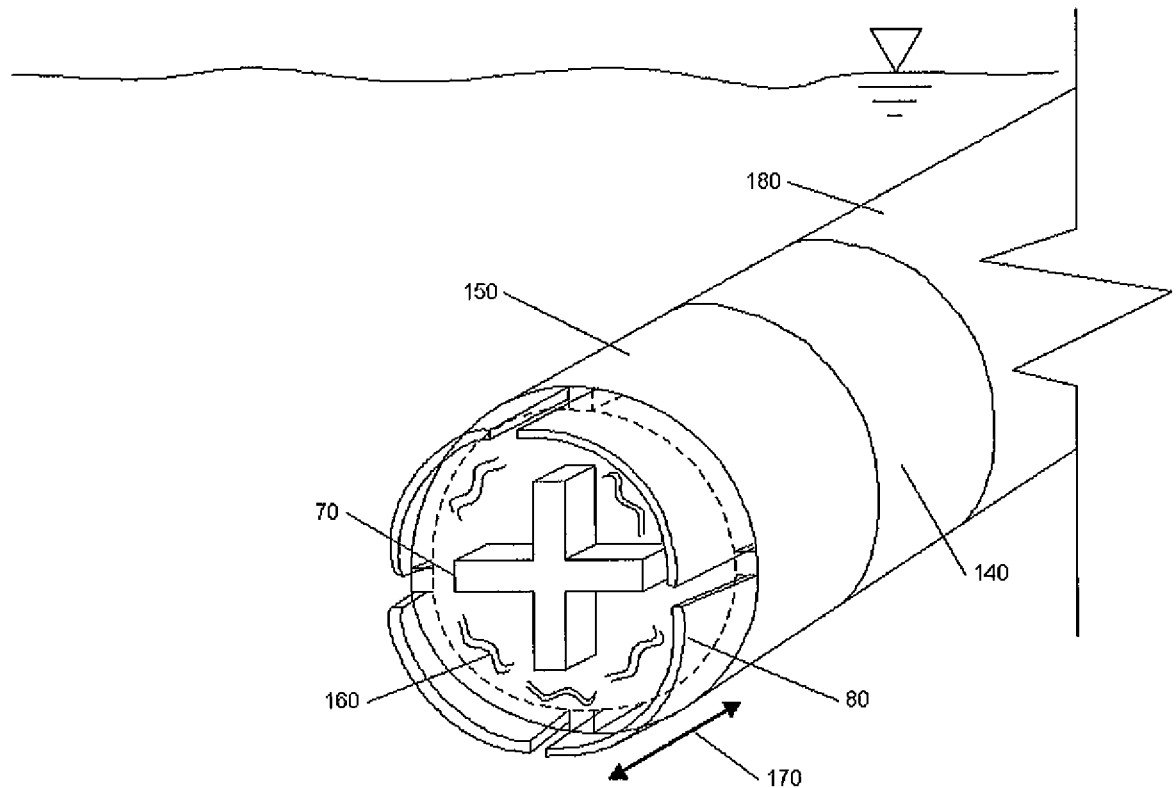
FIG. 3 is an isometric view of the retractable sheath of FIG. 2 disclosing a fluid chamber that activates the acid-base throttle effect of oxy-hydro combustion in an aqueous ionic solution.

FIG. 3 illustrates another view of a preferred embodiment of the acid-base throttling sheath. In this view acid-base throttle sheath mechanism 80 is in the distally extended position. Freedom of travel is shown by translation direction arrows 170. The electrical circuit is completed between active electrode 70 and return electrode 140. Both the active and return electrodes are conductively isolated from each other using thermal and electrical insulator 150 which may preferably be constructed of a ceramic or high temperature polymer. The remaining area of the return electrode is insulated by insulating sheath 180. As depicted, the energy applied to the probe is only sufficient to generate electrolysis and is fully consumed by said reaction, Insufficient excess energy exists to ignite the co-mingling oxy-hydrogen gases and thus only the products of the first of reactions 10 are created. During typical application of low-level RF energy acid-base pair density streak lines 160 are plainly visible to the naked eye; these are byproducts of the electrolysis reactions known to govern the overall process.

The translating sheath 80 may be cylindrical, as depicted, or may be conical, or may alternatively have a conical or cone tip. In this way, the size of the probe may be reduced, and the shape or configuration of the electrodes and sheath may be such as to direct energy in a desired pattern or manner, so as to provide maximal energy delivery to a discrete area to be treated, while minimizing injury to adjacent tissues. Similarly, in this way energy may be directed to the area to be treated without the probes or electrodes actually contacting such area.

In the operation of the preferred embodiment of FIGS. 2 and 3 the oxy-hydro combustion process is mechanically adjusted to suit the desired intensity of operation. Active electrode 70 generates the oxy-hydro combustion reaction, while translating sheath 80 can be positioned to create a convection trap for acid-base pairs 160 generated as part of the oxy-hydro combustion reaction process. Increasing the concentration of the acid-base pairs reduces the net available oxygen and hydrogen gases that can be generated by the electrolysis reaction. This, in turn, leads to a decreased intensity of the overall reaction. This effect is defined herein as the acid-base throttling effect on the oxy-hydro combustion reaction process. The translation of sheath 80 alters the conducted electrical pathway of the RF energy. The sheath, when constructed of a non-metallic substance, does not alter the transmission pathway. By positioning the sheath using ratcheting finger slide 120, coupler guide stanchion 110 and push-rod 100 in combination the oxy-hydro combustion reaction can be trimmed to the most desirable level of intensity. Additionally, in surgical modes of operation where no tissue contact is desired the throttling sheath can be used to fix the distance to the tissue and provide a consistent tissue treatment benchmark distance. When combined with manipulation of delivered power to the active electrode, a precise control of both the oxy-hydro combustion reaction and the surgical process can thus be achieved.

Figure 10:
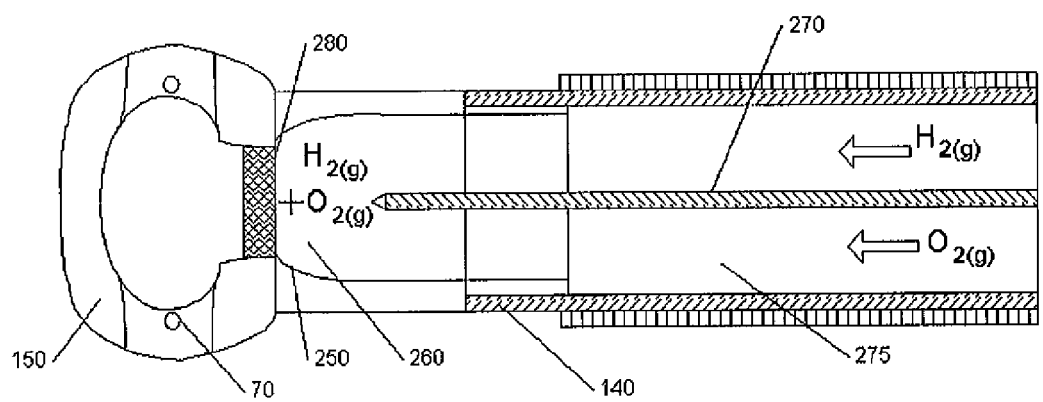
FIG. 10 is a top view of an electrosurgical probe providing conduits for directing the flow of elemental oxygen and hydrogen gases, a co-mingling plenum, and ignition electrode to ignite the oxy-hydro combustion process.
Figure 11:
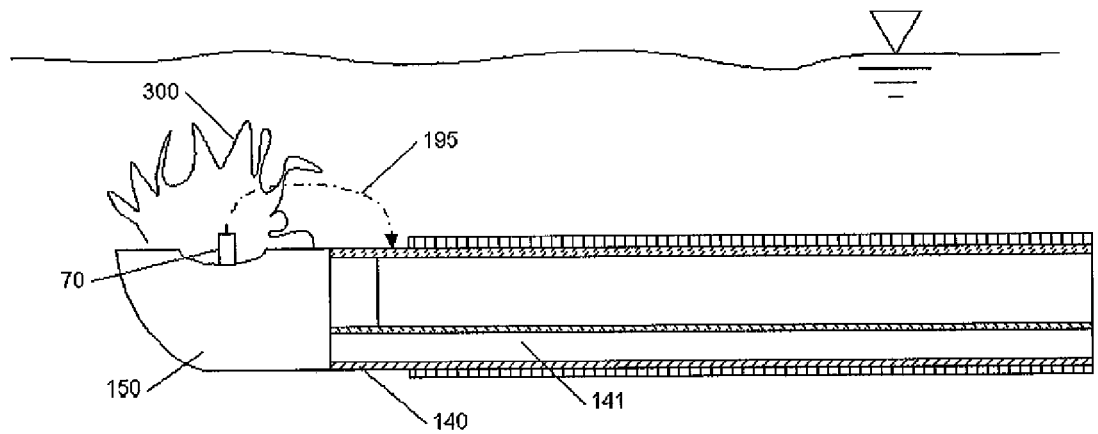
FIG. 11 is a side view of the electrosurgical probe of FIG. 10.

FIGS. 10 and 11 depict a preferred embodiment wherein independent gas flow lumens are provided for the delivery of elemental gases to the probe tip. In this embodiment an electrosurgical oxy-hydro probe provides means for independent delivery of elemental oxygen and hydrogen gas to the probe distal tip reaction zone. Elemental gases are pressure-driven through gas transmission lumen sections 275 separated by gas conduit wall section 270 to prevent premature co-mingling of the elemental gases. Upon exit from the lumen sections the gases are mixed in plenum chamber 260 to facilitate combustion reaction process. The gases are then accelerated through converging nozzle section 250 to enhance dynamic pressure, thereby driving the oxy-hydrogen gas through spark or flame arrester 280. The gas is then channeled upward through insulator 150 toward active electrode 70 to initiate the oxy-hydro combustion reaction process. While an electrode is shown for initiating the oxy-hydrogen gas combustion, it is to be understood that the oxy-hydrogen gas combustion initiation may be from any of a variety of means, such as an electrical spark, mechanical spark, thermal energy transfer and the like. In one particularly preferred embodiment, a piezoelectric gas ignitor may be employed, which may be mechanically or electrically actuated, and which provides a high voltage spark based on the impact of a hammer, such as a spring-driven hammer, on a piezoelectric ceramic substrate. In the case in which an electrode is employed, the voltage and current can be any suitable voltage and current that will initiate a combustion reaction, and the source of power may be either DC or AC. It is to be understood that advantageous, as opposed to prior art electrosurgical devices, the devices described herein do not require an unequal current density between a first electrode and second electrode, and may effectively operate with equal current densities. Similarly, lower energy levels and lower current densities are required than with prior art electrosurgical devices, such energy levels and current densities being only such as are required to initiate combustion of oxygen and hydrogen.

In the embodiment of FIGS. 10 and 11 the need for an electrically conducting irrigant is completely eliminated. FIG. 11 illustrates the separation of the electrical circuit power delivery conduction portion of the probe in isolated electrical channel lumen 141. Active electrode lead wiring traverses the lumen length to the distal portion wherein it is electrically connected to active electrode 70 and can complete a transmission circuit via electromagnetic transmission field lines 195 across insulator portion 150 to return electrode 140. Oxy-hydro combustion zone 300 is created by the ignition of the co-mingled gases being forced from the electrosurgical probe distal tip under fluid pressure. The rate of reaction can be governed by metering of the flow rate of the individual elemental gases or by "starvation" of either elemental gas to run the reaction sub-stoichiometrically "lean" or "rich", which will alter the net heat of reaction according to normal principles of combustion reaction chemistry.

The operation of this embodiment illustrates how the need for a liquid irrigant medium can be completely eliminated. Pressurized elemental oxygen gas and hydrogen gas are independently delivered to probe tip insulator 150 via isolated lumen section 275 and after mixing are ignited by heat generated at active electrode 70 from solid/fluid interface transmission wave generation heating. The intensely hot flame generated can be used for a variety of purposes in a surgical setting. Additional advantages in this specific mode of operation become evident. The power needed to ignite the co-mingling oxy-hydrogen gas mixture is reduced because the conducted portion of the energy needed to electrolyze is now no longer necessary. Only that portion of the energy that provides heating to the active electrode sufficient to ignite the mixture is necessary to sustain the combustion. FIG. 11 illustrates uses in conjunction with a fluid irrigant that provides further enhancing capability to the oxy-hydro combustion reaction process. In many cases having intense heat sources within the human body is undesirable, and use of an irrigant can provide multi-faceted additional advantages, the most apparent of which is as a quenching media to reduce collateral heat transfer to healthy tissue structures. Such an irrigant is preferably composed of acid buffering agents that form a solution resistant to change in pH when either acid or base is added, such as from the natural process of oxy-hydro combustion.

Figure 12:
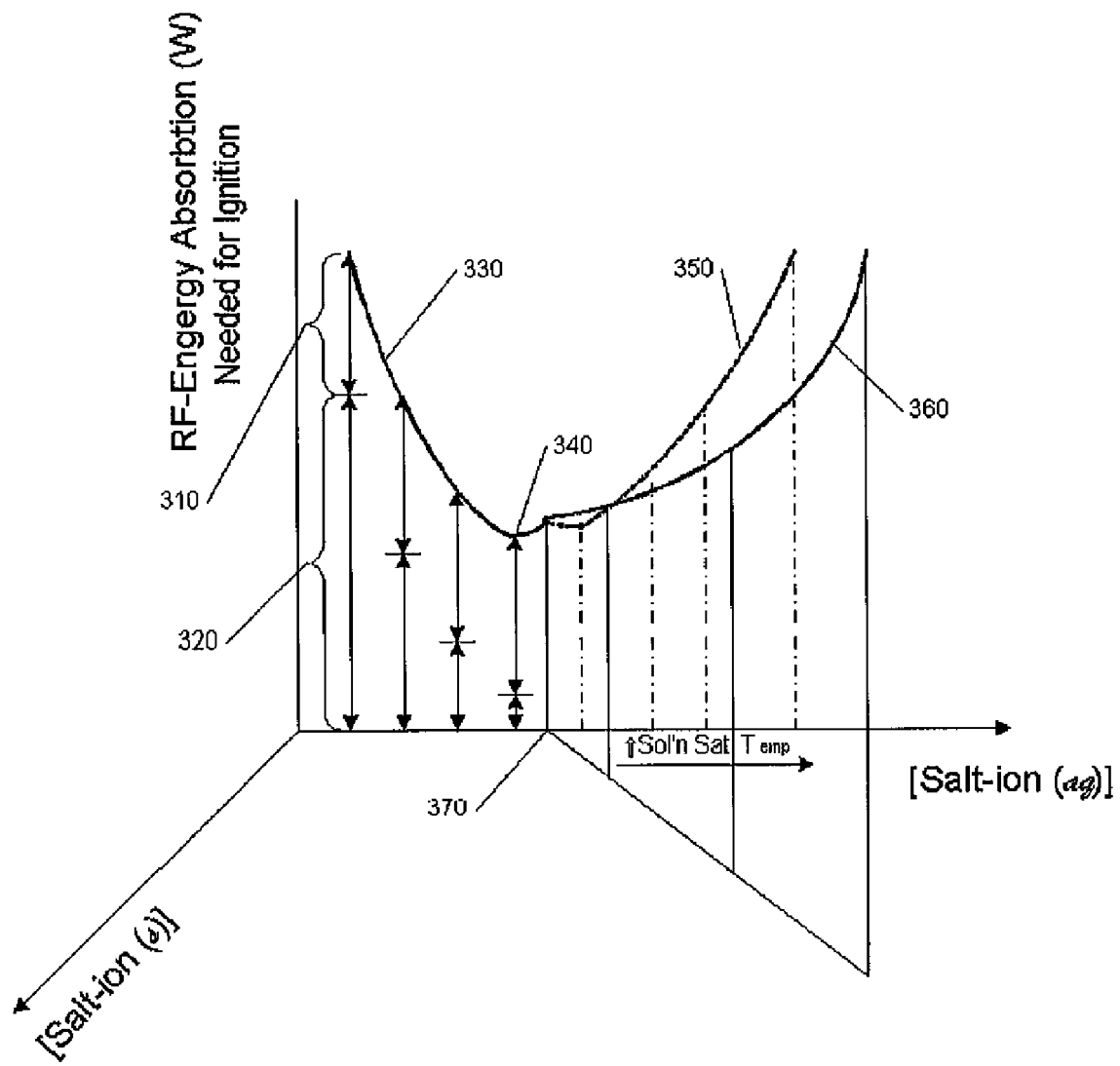
FIG. 12 is a graph depicting the acid-base throttle effect and its relation to salt concentration, energy imparted to the fluid, salt crystal precipitate partial fraction, and electrical conduction.

FIG. 12 depicts the general energy absorption curve for the electrolysis and ignition of the oxy-hydro combustion reaction process. The curves depicted show the multi-dimensional aspects of the immersed environment and how they affect the overall combustion process. It is important to understand that the net energy consumption of the entire process consists of two distinct components of RF energy, conduction and transmission. Conducted energy 320 is consumed in the molecular electron transfer between ions in solution. Transmitted energy 310 involves the electromagnetic wave function that is typically involved with radio-wave transmission. Both elements are present in ambient air, underwater, cellular, and biologic electrosurgery and contribute separate and discrete energy functions to the overall process. As shown in FIG. 12 the mode of energy consumed is dependent on the relative concentration of salt ion in solution. As the salt ion concentration approaches zero the bulk of the energy is consumed through conduction as pure water is only moderately conductive. Some transmission 310 actually occurs at all states and is therefore shown as a smaller portion of the overall energy consumed. As salt ion concentration increases the solution resistivity drops and the amount of energy consumed through conduction 320 also drops. Sufficient resistivity of the solution media remains that heating takes place as part of the conduction process, but the active electrode being heated by its own metallic resistance at the liquid-metal interface delivers the majority of the heat generated prior to ignition of oxy-hydro combustion reaction. As the salt ion concentration continues to increase, conduction resistivity continues to drop until a relative minimum of conduction resistivity 340 is achieved. At this point in oxy-hydro combustion energy absorption process curve 330 the majority of the energy consumed is through transmission 310. In all cases the curve defines the total energy input for which oxy-hydro combustion ignition can be achieved. However, at the optimum salt ion concentration point 340 the minimum amount of input energy is required to both electrolyze the solution and ignite the oxy-hydro combustion reaction.

If the salt ion concentration is increased further still, while holding the solution temperature constant, a partial fraction of solid salt ion will co-exist as a suspension, the overall solution having reached saturation limit 370 for the given temperature. Curve portion 360 illustrates the energy absorption required for oxy-hydro combustion ignition as the partial fraction of salt ion is increased beyond saturation limit 370 for the solution. As the salt ion concentration is increased beyond saturation limit 370 along curve 360, both conduction and transmission resistivity are generally increased and the net energy required to achieve oxy-hydro combustion ignition is also increased. Curve 350 illustrated the shift in solubility created by increasing solution temperature. Temperature rise in solvent is known to increase solute capacity; this condition is commonly referred to as "super-saturation." As the solution is heated, whether artificially or purely by conducted heating from the active electrode, the energy required for oxy-hydro combustion is increased. From equations 10, it can be seen that this is a result of greater concentration of salt ion fraction in the equilibrium state of acid-base pairs, which reduce the net amount of water that can be electrolyzed into oxygen and hydrogen gases. This specific condition is an artifact of a finite reservoir. In many surgical situations, as the fluid is in constant flow there is no excessive buildup of acid-base pairs, since they are "flushed" away in the flowing solution.

It can be appreciated from the chart in FIG. 12 that the acid-base throttle effect can be overcome through the addition of RF energy as the concentration of acid-base in solution rises. This is most advantageous in understanding why maintaining an optimum flow throughout the surgical field proves beneficial in electrosurgery. Too much flow and the heated buoyant gas escapes more rapidly than it can be combusted and becomes useless to the surgical process. On the other extreme too little or no flow leads to excessive heating and build-up of acid-base that can have deleterious tissue effects if left to accumulate for an extended period, including tissue and nerve damage or necrosis. The graph reveals that the solution temperature will have an indirect performance effect in allowing probe operations that vary widely from the optimum energy minima of concentration point 340.

Figure 13:
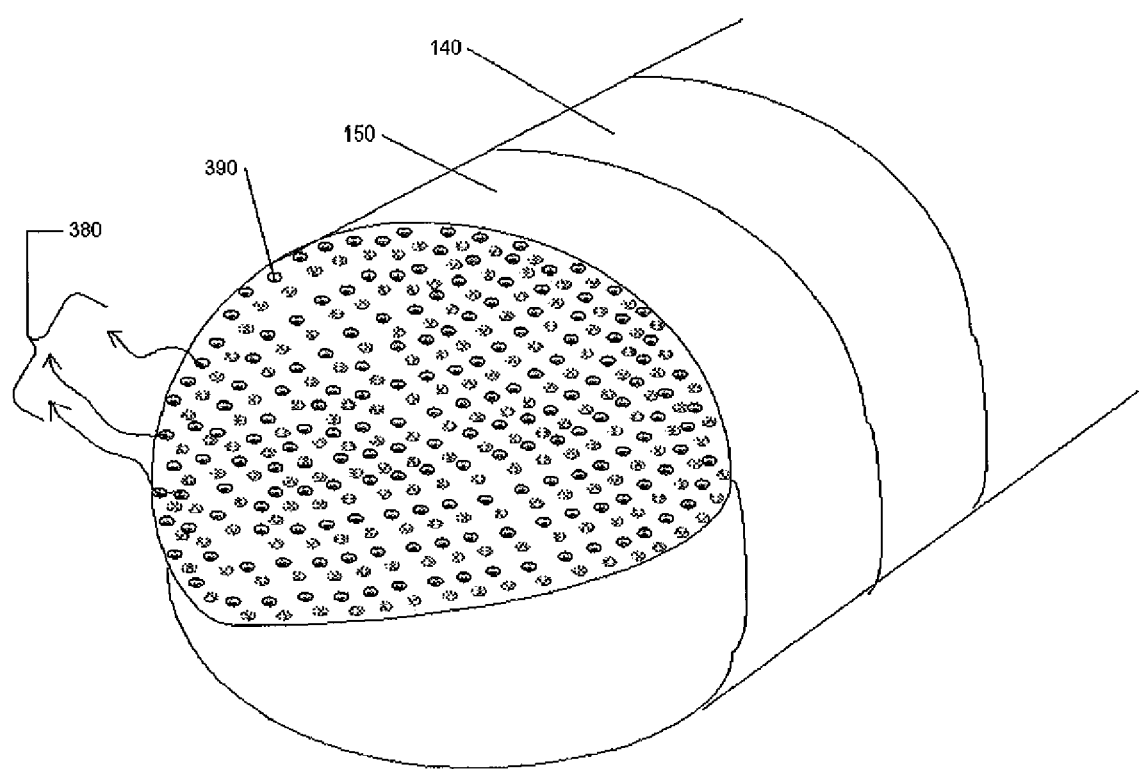
FIG. 13 is a view of a porous electrode used to meter the flow of oxygen, hydrogen or co-mingled enriching gases.

FIG. 13 is a view of an embodiment wherein the active electrode includes a porous gas-liberating alloy. Elemental gas is delivered under positive pressure to active electrode 390 and forced through pores in the conductor. The enriching gas stream exits in diffuse gas stream 380 and enters the oxy-hydro combustion zone. Electromagnetic energy is sufficiently imparted to the combustion zone to liberate elemental gas from the electrode alloy and ignite the enriched co-mingled mixture. The electromagnetic energy is delivered in transmission from active electrode 390 to return electrode 140, which is both thermally and electrically insulated by insulator 150. Insulator 150 can preferably be made from high temperature refractory ceramics or ceramic alloys. Elemental diffuse gas stream 380 is comprised of molecular hydrogen gas, molecular oxygen gas, or co-mingled oxygen and hydrogen gases to enrich the oxy-hydro combustion zone.

In mode of operation of the device of FIG. 13, several of the independent elements have been combined into a configuration of an electrosurgical probe including porous active electrode 390, which may but need not include a gas-liberating alloy, to enhance the oxy-hydro combustion reaction process. Probe activation is enhanced by forcing elemental gas 380 through the pores of active electrode 390 into the oxy-hydro combustion zone for either quenching or maximizing heat of the oxy-hydro combustion reaction. The pores of active electrode 390 allow multi-variate functions, including metering, mixing and directing the elemental enriching gases to the combustion zone. This embodiment provides improved fluid dynamics at the surface of active electrode 390, including a laminar flow of the ejecting gas or gases, more even distribution of the gas or gases and rapid thermal quench characteristics. When operated in underwater, cellular and biologic surgical environments the embodiment of FIG. 6 provides means for improving the combustion zone dynamic volume by preventing pressure field variations from forcing the collapse of the gas volume and quenching the electrode, thereby preventing oxy-hydro combustion. By supplying a uniform gas field immediately above the active electrode the gas volume is created as much by the flowing of the pressurized gas as by the electrolysis of the salt ion solution. This lowers the net power required to achieve ignition of the gas mixture and provides means for operating at much lower power levels, until a spike of energy is applied whereupon a pulse of oxy-hydrogen gas is supplied to active electrode 390, creating conditions for an oxy-hydro combustion reaction cascade. From this description it will become apparent to those skilled in the art that many dynamic controls can be used to govern the flow of gas in concert with the power output delivered to the active electrode to achieve novel effects in the oxy-hydro combustion zone.

It is to be understood that any of the devices as described above may employ a fuel cell to produce electrical power. In one preferred embodiment, a proton exchange membrane type of fuel cell is employed, wherein hydrogen and optionally also oxygen is provided by means of one or more canisters, which canisters are optionally further employed for oxy-hydrogen combustion. It is to be understood that if the device employs an active electrode, such that electrolysis and combustion are both simultaneously induced, that excess hydrogen so produced may be employed, in whole or in part, for such fuel cells, or alternatively other sources of hydrogen, such as a storage canister, may be employed. Oxygen may alternatively be obtained from the atmosphere. Sufficient separate fuel cells are combined to form a fuel-cell stack producing the voltage required for the specific application.

The preceding devices can be varied by substituting the generically or specifically described components and/or structures of this invention for those used in the preceding devices.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A movable sheath adapted for use with a radiofrequency (RF) electrosurgical probe, comprising:
   a generally cylindrical plenum with an open first end and an open second end and of a diameter such that the open second end may be co-axially placed over the electrode end of an RF electrical probe, whereby the open first end extends beyond the electrode end of the RF electrical probe; and
   a flexible polymeric fixation sleeve for securing the position of the RF electrosurgical probe within the generally cylindrical plenum wherein the generally cylindrical plenum further comprises a plurality of perforations.

2. The sheath of claim 1 wherein the flexible polymeric fixation sleeve is fixed to the generally cylindrical plenum.

3. A movable sheath adapted for use with a radiofrequency (RF) electrosurgical probe, comprising:
   a generally cylindrical plenum with an open first end and an open second end and of a diameter such that the open second end may be co-axially placed over the electrode end of an RF electrical probe, whereby the open first end extends beyond the electrode end of the RF electrical probe; and
   a flexible polymeric fixation sleeve for securing the position of the generally cylindrical plenum to the RF electrosurgical probe wherein the movable sheath comprises a plurality of demarcations for determining the position of the movable sheath with respect to the electrode end of the RF electrical probe.

* * * * *